(12) United States Patent
Winqvist et al.

(10) Patent No.: US 11,059,846 B2
(45) Date of Patent: **\*Jul. 13, 2021**

(54) IMMUNE STIMULATING COMPOUND

(71) Applicant: ISR IMMUNE SYSTEM REGULATION HOLDING AB (PUBL), Stockholm (SE)

(72) Inventors: Ola Winqvist, Uppsala (SE); Emma Lindh, Knivsta (SE); Robert Wallin, Bålsta (SE); Matt Gregory, Cambridge (GB); Steven Moss, Cambridge (GB)

(73) Assignee: ISR IMMUNE SYSTEM REGULATION HOLDING AB (PUBL), Solna (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/487,813

(22) PCT Filed: Feb. 22, 2018

(86) PCT No.: PCT/EP2018/054340
§ 371 (c)(1),
(2) Date: Aug. 21, 2019

(87) PCT Pub. No.: WO2018/153957
PCT Pub. Date: Aug. 30, 2018

(65) Prior Publication Data
US 2020/0010499 A1 Jan. 9, 2020

(30) Foreign Application Priority Data

Feb. 22, 2017 (EP) .................................... 17157387

(51) Int. Cl.
| | |
|---|---|
| *A01N 43/04* | (2006.01) |
| *A61K 31/70* | (2006.01) |
| *C07H 17/08* | (2006.01) |
| *A61P 31/04* | (2006.01) |

(52) U.S. Cl.
CPC .............. *C07H 17/08* (2013.01); *A61P 31/04* (2018.01)

(58) Field of Classification Search
None
See application file for complete search history.

(56) References Cited

FOREIGN PATENT DOCUMENTS

| | | |
|---|---|---|
| EP | 1350510 A1 | 10/2003 |
| WO | 2005054265 A2 | 6/2005 |

OTHER PUBLICATIONS

International Search Report of the International Searching Authority for Application No. PCT/EP2018/054340, dated Jun. 6, 2018, 6 pages.
Written Opinion of the International Searching Authority for Application No. PCT/EP2018/054340, dated Jun. 6, 2018, 9 pages.
International Preliminary Report on Patentability for Application No. PCT/EP20181051340, dated Feb. 13, 2019, 16 pages.

*Primary Examiner* — Patrick T Lewis
(74) *Attorney, Agent, or Firm* — Carl A. Morales; Todd K. Macklin; Dechert LLP

(57) ABSTRACT

The present invention provides immune stimulating macrolide of formula (I). The macrolide has utility in treating intracellular bacterial, fungal, and protozoal infections.

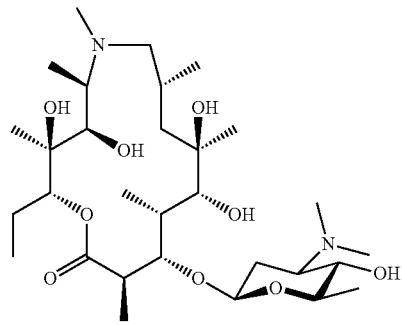

(I)

10 Claims, 16 Drawing Sheets
Specification includes a Sequence Listing.

Figure 8:
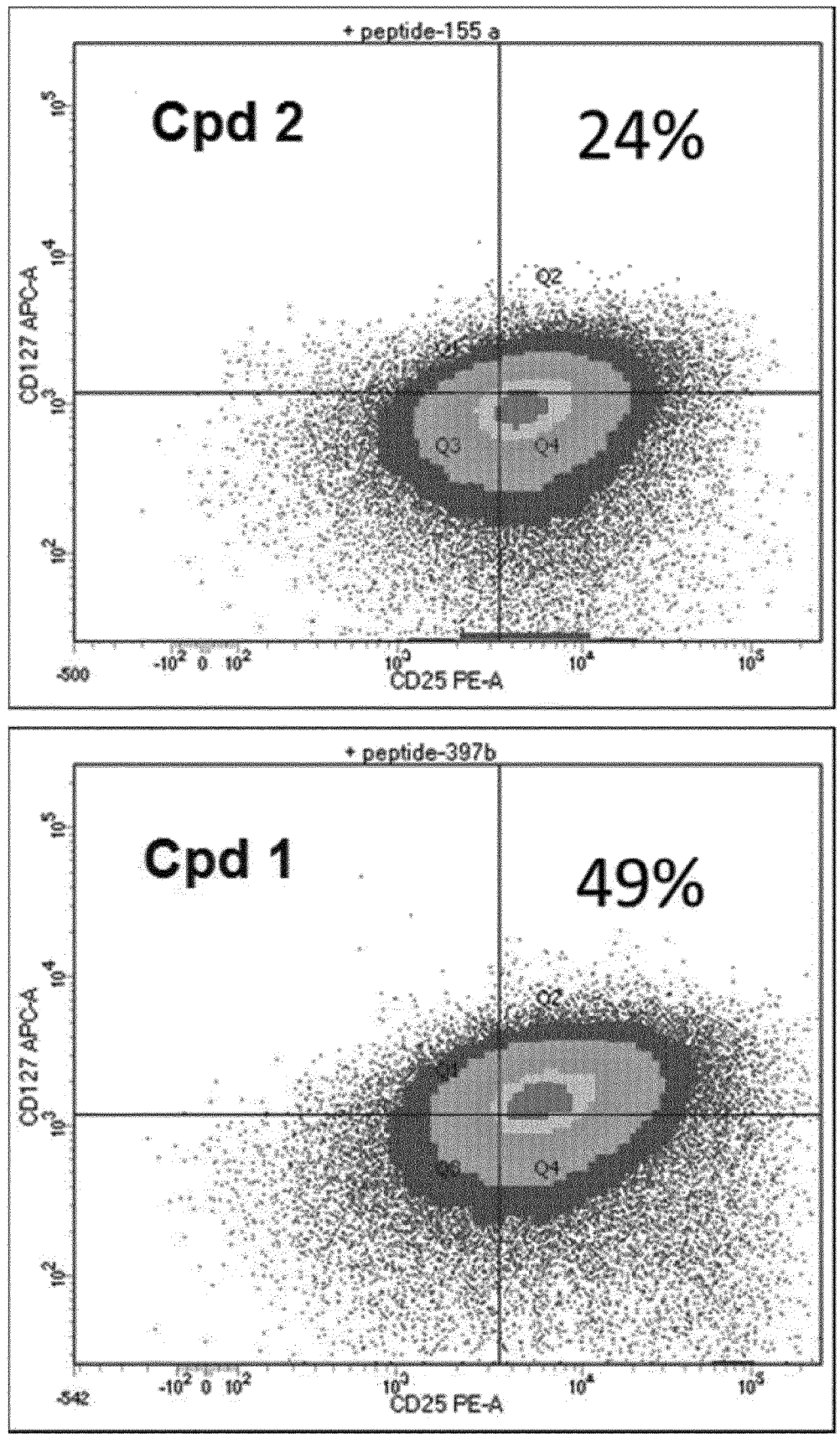

Figure 8 - continued
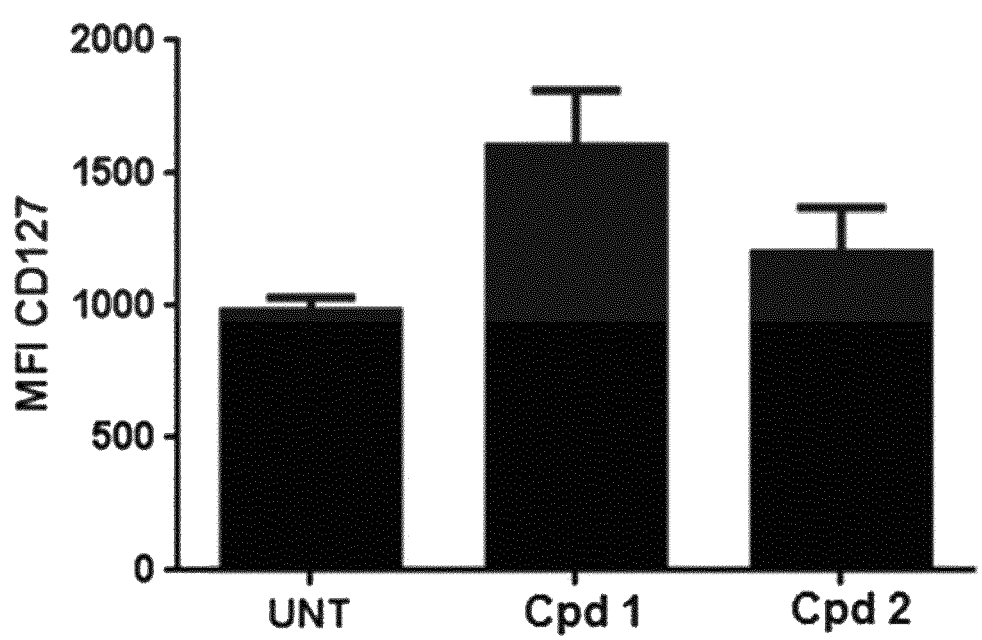

IMMUNE STIMULATING COMPOUND

FIELD OF THE INVENTION

The present invention provides a novel macrolide compound capable of stimulating the immune system. The present invention relates to a novel compound for use in medicine, notably in the treatment of intracellular bacterial, fungal, and protozoal infections and in the co-treatment of viral disease, chronic inflammatory conditions, and cancer when stimulation of the immune system is beneficial. The compound may also be used as immune modulating adjuvants in vaccination. The novel macrolide maximizes the modulating effects of the immune system while minimizing the therapeutically unwanted direct antibacterial effects. The present invention also provides methods for preparing the compound of the invention and for use of the compound in medicine.

BACKGROUND OF THE INVENTION

Intracellular bacterial, fungal, and protozoal infections are often not diagnosed in healthy individuals as they appear asymptomatic, or because the symptoms are mild enough that the infected individual is not inclined to seek medical assistance. As such, intracellular infections may persist latently or may progress to a disease state. Conditions interfering with normal T cell function usually leads to progression of the disease from a latent infection, and intracellular infections such as *Mycobacterium tuberculosis* (Mtb) are a common cause of death in patients where HIV infection has progressed to AIDS. There is thus a great need in the art for methods and means of treating intracellular infections.

Intracellular pathogens such as Mtb have the capacity to hide within intracellular compartments in monocytes and macrophages causing persistent infections. Although Mtb are recognized by CD4$^+$ T helper cells in the lung and an appropriate response is mounted, the system fails to create sterilizing immunity (MacMicking 2012).To escape immune recognition by the host, Mtb have developed a series of mechanism that inhibits recognition of Mtb peptides presented in the MHC class II pocket for CD4$^+$ T helper cells. Toll like receptor 2 has been demonstrated to be inhibited by Mtb, which in turn inhibits IFN-γ induced MHC class II expression (Noss 2001). In addition, data suggest that Mtb has the capacity to inhibit phagosome processing and maturation, possibly by an invariant chain associated mechanism (Ramachandra 2001). Therefore, the normal antigen processing, loading and presentation of MHC class II peptides derived from Mtb is impaired due to Mtb produced immune escape factors.

The endosomal lysosomal pathway is designed to take up pathogens, process them into 12-15 aa long peptides, peptides, that after the removal of the Invariant chain peptide CLIP by HLA-DM, are loaded into the MHC class II pocket. The antigen loading is followed by transport of the MHC class II-peptide complex to the cell surface for presentation for the specific T cell receptor of CD4$^+$ T helper cells (Roche 2015). Recently the Mtb expressed protein EsxH has been reported to directly inhibit the endosomal sorting complex required for transport (ESCRT) machinery (Portal-Celhay 2016). EsxH inhibits the ability of antigen presenting monocytes and macrophages to activate CD4$^+$ T helper cells. Since intact ESCRT machinery seems necessary for antigen processing, presentation and activation of T cells, EsxH is the link that explains Mtb induced immune escape by intervening with the MHC class II pathway.

The importance of MHC class II presentation has also been demonstrated in patients with primary immunodeficiencies (PID). PID patients with defects in the IFN-γ circuit, involving IFNGR and IL-12, have an increased risk of acquiring TBC and atypical mycobacterial infections. Since MHC class II expression is dependent upon and regulated by IFN-γ expression defects in the IFN-γ circuit will result in additionally decreased MHC class II expression and a poor activation of CD4$^+$ T helper cells.

Protozoa such as *Toxoplasma gondii* have developed a mechanism to avoid immune recognition by hiding intracellularly as an obligate intracellular parasite. The mechanism involves interference with MHC class II expression and thus diminishes the amount of *Toxoplasma gondii* to be presented for specific CD4$^+$ T helper cells. The detailed mechanism is dependent on soluble proteins expressed by *Toxoplasma gondii* that inhibit IFN-gamma induced expression of MHC class II (Leroux 2015).

Furthermore, it has been demonstrated that different fungal infections are dependent on MHC class II expression. *Cryptococos neoformans* may cause life threatening brain infections in patients with immunodeficiencies including HIV. Work in a mouse model of *Cryptococos neoformans* infection has demonstrated that the activation of microglial cells and their upregulation of MHC class II, in an IFN-gamma dependent manner, is critical for survival (Zhou 2007).

Therefore, to overcome the immune escaping mechanisms induced by Mtb and other intracellular bacteria, protozoa such as *Toxoplasma gondii*, or fungi exemplified by *Cryptococcus*, an increased expression of MHC class II and MHC class I on the cell surface of monocytes, macrophages, microglia, or other infected cells is likely beneficial for immune recognition and elimination of the pathogen.

Macrolides, such as erythromycin and azithromycin, have been used for years in the treatment of bacterial infections. Erythromycin is a polyketide natural product macrolide produced by fermentation of the actinomycete *Saccharopolyspora erythraea*. Azithromycin is a semisynthetic azalide derivative of erythromycin. Many references exist describing the antibacterial activity of macrolides, such as erythromycin. This antibacterial mechanism is achieved through molecule binding to the P-site on the bacterial 50S bacterial ribosome, thus interfering with the tRNA binding.

Many references describe generation of analogues of erythromycin via semisynthesis and biosynthetic engineering. In particular, methods have been described for semi-synthetic removal of the glycosyl groups on erythromycin, desosamine and mycarose/cladinose. Further methods have been described for biotransformation to add alternative glycosyl groups to the erythromycin aglycone (e.g. see Gaisser et al., 2000, Schell et al., 2008 and WO2001079520). The main focus of this published work, however, has been to generate antibacterial erythromycin analogues.

DESCRIPTION OF THE INVENTION

Figure 4:
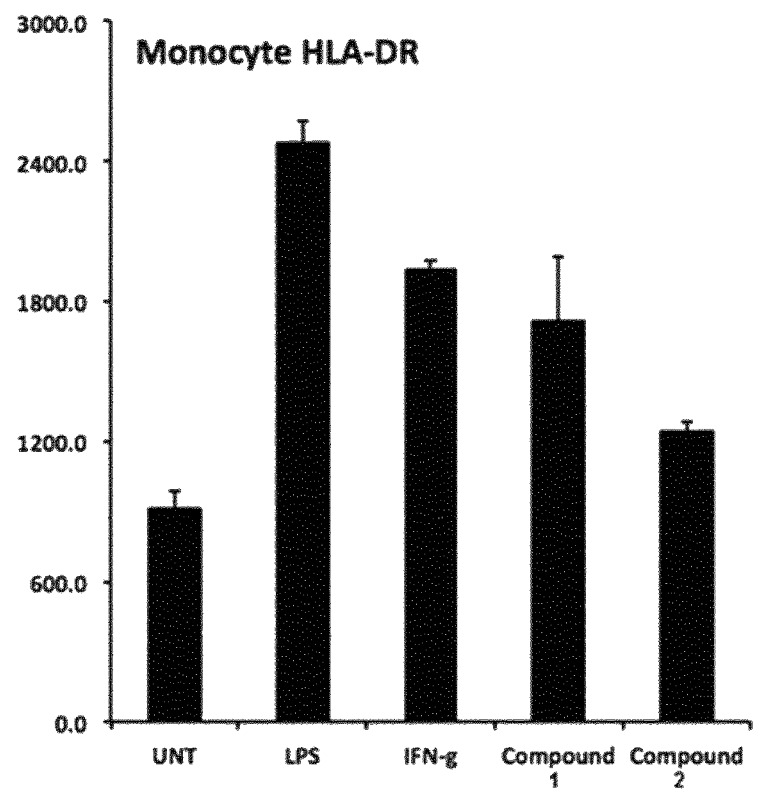
Figure 4:
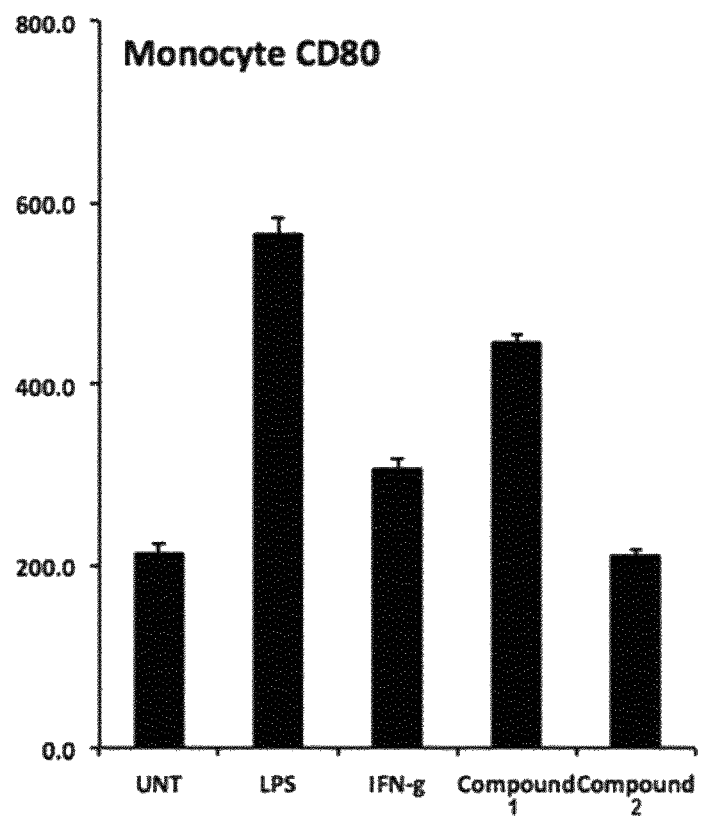
Figure 5:
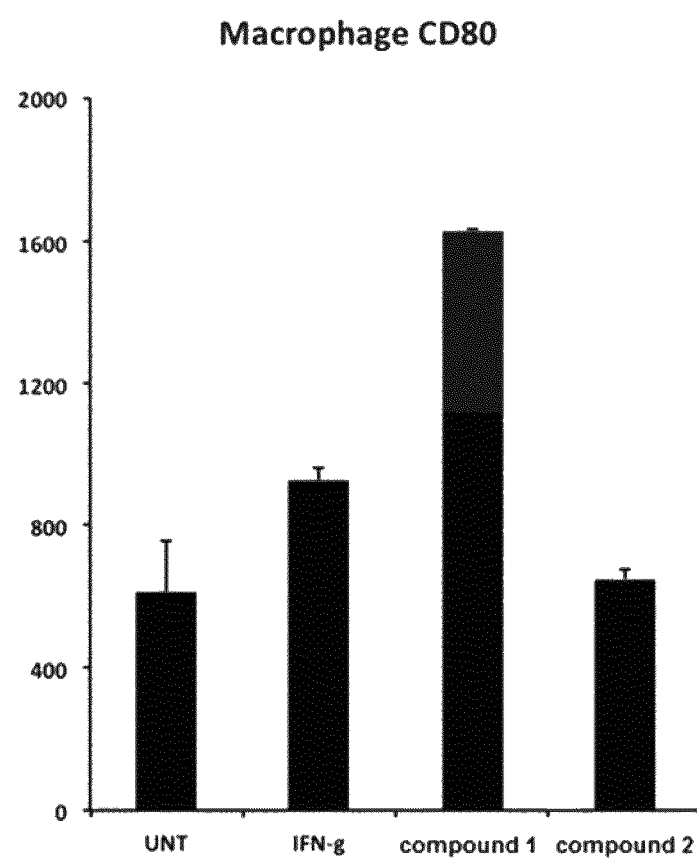
Figure 6:
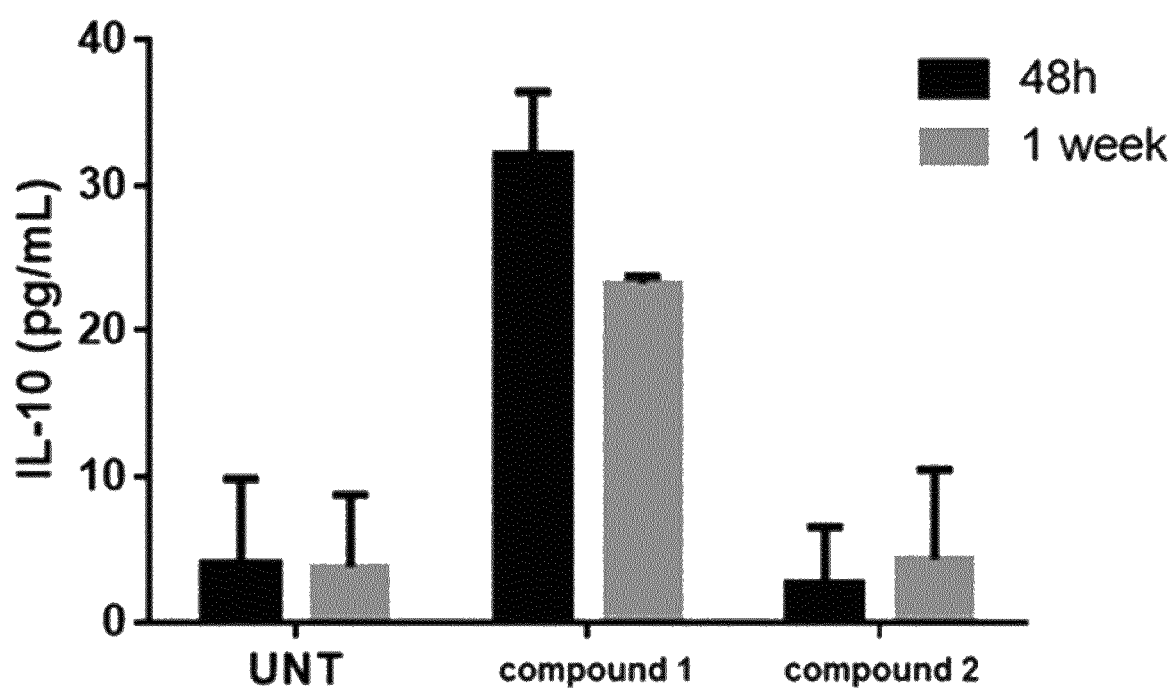
Figure 7:
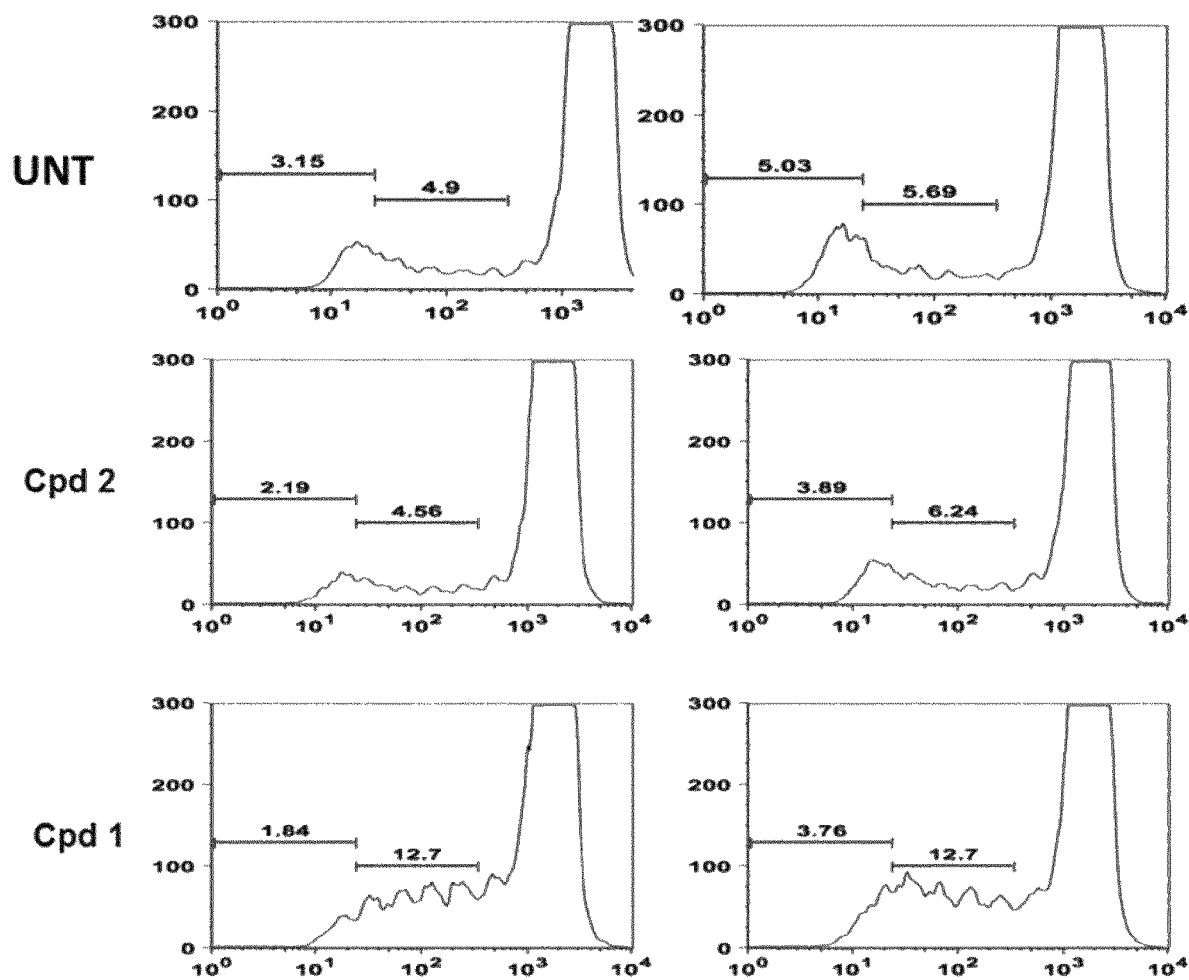

Immune stimulating activity from macrolides that lack direct antibacterial activity has previously not been reported. Surprisingly, we found that a compound of the invention (compound 1, FIG. 1) had a potent immune stimulating effect on several cell types of the immune system. After 24-48 h of in vitro stimulation of peripheral blood mononuclear cells (PBMC) with 1 μM compound 1 (FIG. 1) the activation marker CD69 was upregulated on CD4 T cells and B cells (FIG. 2). We also observed upregulation of the MHC class I molecule (HLA-ABC) on T- and B-cells (FIG. 3), indicating an effect on antigen presentation of antigens derived from intracellular infections. Stimulation of monocytes in the PBMC population with compound 1 led to the upregulation of the costimulatory molecule CD80 as well as the antigen presenting molecule MHC class II (HLA-DR) (FIG. 4). Monocytes differentiated into macrophages also upregulated CD80 in response to stimulation by compound 1 (FIG. 5). Furthermore, PBMCs stimulated with compound 1 expressed an altered cytokine profile with increased production of the immunosuppressive cytokine IL-10, indicating an immune inhibitory effect under certain conditions (FIG. 6). Further analysis of the immunological effect of compound 1 revealed an altered cytokine driven proliferation profile of T cells after six days stimulation, measured with flow cytometry (FIG. 7). In addition, virus specific T cell proliferation was affected by compound 1. PBMCs from cytomegalovirus (CMV) infected donors cultured in the presence of CMV antigen and compound 1 displayed an altered phenotype of activated CMV specific CD8+ T cells with an increased expression of IL-7 receptor a (CD127) (FIG. 8). CD127 is crucial for T cell homeostasis, differentiation and function, and reduced expression correlates with disease severity in HIV and other chronic viral diseases (Crawley et al Sem Imm 2012). In summary, compound 1 has a surprising ability to specifically activate and modify an immune response by affecting antigen presentation, co-stimulation and T cell activation and proliferation. In many of these studies, compound 2, another related macrolide erythromycin analogue with altered glycosylation, previously published in Schell et al. 2008 (as compound 20), was included as it showed little or no activity in the assays.

Thus, in one aspect of the invention there is provided an immune stimulating macrolide of Formula (I) (also known as compound 1) without substantial antibacterial activity as defined herein:

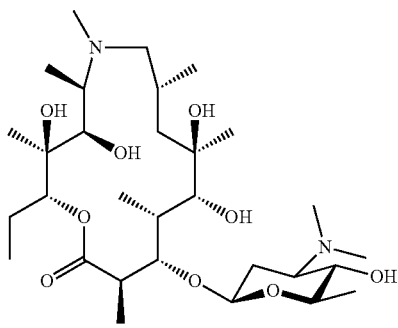

Formula (I)

Within the scope of the present invention is also compounds of Formula (I) or a pharmaceutically acceptable salt, hydrate, solvate, tautomer, enantiomer or diastereomer thereof.

In another aspect of the invention, there is provided a method for producing a compound of formula (I), which involves addition of an aglycone with formula II to a culture of a biotransformation strain which glycosylates at the 3-hydroxyl position.

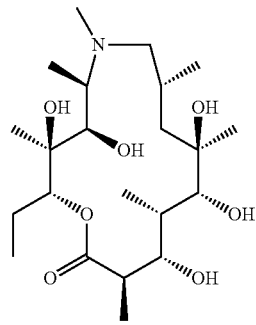

Formula II

In a preferred embodiment of this invention, the biotransformation strain expresses glycosyltransferases with 70% or more homology to AngMII (SEQ ID no. 1) or AngMIII (SEQ ID no. 2), such as with 75% or more, with 80% or more, with 90% or more or with 95% or more homology such as 100% homology.

The homology between two amino acid sequences or between two nucleic acid sequences is described by the parameter "identity". Alignments of sequences and calculation of homology scores may be done using e.g. a full Smith-Waterman alignment, useful for both protein and DNA alignments. The default scoring matrices BLOSUM50 and the identity matrix are used for protein and DNA alignments respectively. The penalty for the first residue in a gap is −12 for proteins and −16 for DNA, while the penalty for additional residues in a gap is −2 for proteins and −4 for DNA. Alignment may be made with the FASTA package version v20u6. Multiple alignments of protein sequences may be made using "ClustalW". Multiple alignments of DNA sequences may be done using the protein alignment as a template, replacing the amino acids with the corresponding codon from the DNA sequence. Alternatively, different software can be used for aligning amino acid sequences and DNA sequences. The alignment of two amino acid sequences is e.g. determined by using the Needle program from the EMBOSS package (http://emboss.org) version 2.8.0. The substitution matrix used is BLOSUM62, gap opening penalty is 10, and gap extension penalty is 0.5.

General Chemistry Methods

The skilled person will recognise that the compound of the invention may be prepared, in known manner, in a variety of ways. The routes below are merely illustrative of some methods that can be employed for the synthesis of compounds of formula (I).

In one general route erythromycin A is subjected to semisynthetic manipulation to generate azithromycin. Methods for this transformation are known (U.S. Pat. Nos. 3,478,014; 4,328,334; and 4,474,768; Glansdorp et al. 2008), though variants on these routes or other routes may be used to the same purpose. The mycarose/cladinose and/or desosamine are removed by further chemical methods, such as glycoside cleavage. Briefly, in one method the sugars may be removed by treatment with acid. In order to facilitate removal of the amino sugar it is first necessary to oxidise the dimethylamine to form an N-oxide which is then removed by pyrolysis. The resultant 5-O sugar, and 3-O sugar, can then be removed by acidic degradation. A suitable method is taught by LeMahieu (1974) and Djokic, S., et al., (1988). Finally, the compound is biotransformed using a bacterial strain which adds the amino sugar.

General use of the Compounds of the Invention

The compound as described herein can be used in medicine, medical research or in the manufacture of a composition for such use. Accordingly, when in the following the term "compound of the invention" is used in connection with medical use or pharmaceutical composition, the term is intended also to include the compound of formula (I) provided that this compound has not been known for such a use.

The compound of the invention is designed in order to minimize direct antibacterial effects, but rather focus on immune activating properties. When compound 1 is added to cultures of bacteria *E. coli, S. salivarius, L. casei, B. longum* or *M. luteus* no or minimal antibacterial effect is recognized. The advantage of having a compound with isolated immune stimulatory properties that effect the host cells is that development of bacterial resistance is avoided. In addition, the well-known side effect of macrolides affecting the gut microbiota, with the risk of overgrowth of *Clostridium difficile* causing diarrhea and *pseudomebraneous colitis*, is avoided. Many intracellular pathogens such e.g. Mtb, as well as viruses and cancers have developed mechanisms to avoid immune recognition, i.e. by down regulating HLA expression, to avoid detection by T cells. The mechanism of the compound of the intervention rely on the activation and increased expression of HLA molecules on infected cells. HLA molecules load and present peptides derived from intracellular infectious agents in order to present a recognition signal for T cells allowing elimination of infected cells.

The compound of the invention disclosed herein may be used in the treatment of intracellular bacterial, fungal, and protozoal infections, such as bacterial infections caused by *Mycobacterium tuberculosis, Mycobacteria* causing atypical disease, *Mycobacterium avium* and *M. intracellulare* (also known as *Mycobacterium avium*-intracellulare complex, or MAC), *M. kansasii, M. marinum, M. fortuitum, M. gordinae, Mycoplasma pneumoniae, M. genitalium, M. hominis, Ureaplasma urealyticum, U. parvum, Chlamydophila pneumoniae,* and *Salmonella typhimurium*, such as protozoal infections caused by *Toxoplasma gondii, Plasmodium falciparum, P. vivax, Trypanosoma cruzi, Cryptosporidium*, and *Leishmania*, and such as fungal infections caused by Histoplasma capsulatum,

*Cryptococcus neoformans*, and *Encephalitozoon cuniculi*.

The compound of the invention may be used treatment of intracellular bacterial, fungal, and protozoal infections when these infections occur alone or in association with viral agents or viral disease or in association with other causes of primary or secondary immunodeficiency. Causes of primary immunodeficiency include inherited genetic deficiencies and somatic mutations, whereas secondary immunodeficiency may be caused by viral infections such as those described above, or by inheritable or non-inheritable conditions such as diabetes mellitus, or malnutrition, or by agents such as immunodepressants, drug abuse, or other environmental factors.

Moreover, the compound of the invention may be used as a treatment or co-treatment for diseases, disorders, conditions, and symptoms, where immune response stimulation is useful, such as in treating patients infected with viral agents or with viral diseases such as HIV, Adenovirus, Alphavirus, Arbovirus, Borna Disease, Bunyavirus, Calicivirus, Condyloma Acuminata, Coronavirus, Coxsackievirus, Cytomegalovirus, Dengue fever virus, Contageous Ecthyma, Epstein-Barr virus, Erythema Infectiosum, Hantavirus, Viral Hemorrhagic Fever, Viral Hepatitis, Herpes Simplex Virus, Herpes Zoster virus, Infectious Mononucleosis, Influenza, Lassa Fever virus, Measles, Mumps, Molluscum Contagiosum, Paramyxovirus, Phlebotomus fever, Polyoma-virus, Rift Valley Fever, Rubella, Slow Disease Virus, Smallpox, Subacute Sclerosing Panencephalitis, Tumor Virus Infections, West Nile Virus, Yellow Fever Virus, Rabies Virus and Respiratory Syncitial Virus.

Moreover, the compound of the invention is contemplated to be suitable for use in the co-treatment of cancer, in particular Adrenal Cancer, Anal Cancer, Bile Duct Cancer, Bladder Cancer, Bone Cancer, Brain/CNS Tumors, Breast Cancer, Castleman Disease, Cervical Cancer, Colon/Rectum Cancer, Endometrial Cancer, Esophagus Cancer, Eye Cancer, Gallbladder Cancer, Gastrointestinal Carcinoid Tumors, Gastrointestinal Stromal Tumor (GIST), Gestational Trophoblastic Disease, Hodgkin Disease, Kaposi Sarcoma, Kidney Cancer, Laryngeal and Hypopharyngeal Cancer, Acute Myeloid Leukemia, Chronic Lymphocytic Leukemia, Acute Lymphocytic Leukemia, Chronic Myeloid Leukemia, Chronic Myelomonocytic Leukemia, Liver Cancer, Non-Small Cell Lung Cancer, Small Cell Lung Cancer, Lung Carcinoid Tumor, Lymphoma, Malignant Mesothelioma, Multiple Myeloma, Myelodysplastic Syndrome, Nasal Cavity and Paranasal Sinus Cancer, Nasopharyngeal Cancer, Neuroblastoma, Non-Hodgkin Lymphoma, Oral Cavity and Oropharyngeal Cancer, Osteosarcoma, Ovarian Cancer, Pancreatic Cancer, Penile Cancer, Pituitary Tumors, Prostate Cancer, Retinoblastoma, Rhabdomyosarcoma, Salivary Gland Cancer, Basal and Squamous Cell Skin Cancer, Melanoma, Merkel Cell Skin Cancer, Small Intestine Cancer, Stomach Cancer, Testicular Cancer, Thymus Cancer, Thyroid Cancer, Uterine Sarcoma, Vaginal Cancer, Vulvar Cancer, Waldenstrom Macroglobulinemia, and Wilms Tumor.

Thus, the advantageous properties of the compound of the invention over the prior art macrolides may include one or more of the following:

Reduced direct antibacterial activity
Improved MHC class I stimulation
Improved immunomodulation
Improved activation of antigen presenting cells
Improved T-cell response
Improved antiviral activity
Improved MHC class II antigen presentation Pharmaceutical Compositions Comprising a Compound of the Invention The present invention also provides a pharmaceutical composition comprising the compound of the invention together with one or more pharmaceutically acceptable diluents or carriers. Similarly, the present invention also provides a pharmaceutical kit comprising at least one pharmaceutical composition comprising the compound of the invention together with one or more pharmaceutically acceptable excipients. The present invention also relates to cosmetic or veterinary compositions comprising the compound of the invention together with one or more cosmetically or veterinary acceptable excipients.

The compound of the invention or pharmaceutical, cosmetic, or veterinary compositions comprising the compound of the invention may be administered by any conventional route such as but not limited to parenteral, oral, topical, or via a mucosa (including buccal, sublingual, transdermal, vaginal, rectal, nasal, ocular, etc.), via a medical device (e.g. a stent), or by inhalation. The treatment may consist of a single administration or a plurality of administrations over a period of time.

The dosage regimen of the compound of the invention and the pharmaceutical compositions of the invention may be varied depending on the pharmaceutical properties of the compound or composition in question. The dosage regimen may consist of a single administration or a plurality of administrations over one or more periods of time. Administration may be once daily, twice daily, three times daily, four times daily, less frequently, or more frequently, depending on the specific use, the disease to be treated, and the physical condition and characteristics (such as gender, weight, and age) of the patient to be treated. The treatment may also be by continuous administration such as e.g. intravenous administration via a drop or via depots or sustained-release formulations.

Whilst it is possible for the compound of the invention to be administered as such, it is preferable to present it as a pharmaceutical composition together with one or more pharmaceutically acceptable excipients. The excipient(s) must be "acceptable" in the sense of being compatible with the compound of the invention and not deleterious to the recipients thereof. Examples of suitable excipients are described in more detail below.

The pharmaceutical compositions may conveniently be presented in a suitable dosage form including a unit dosage form and may be prepared by any of the methods well known in the art of pharmacy. Such methods include the step of bringing into association the compound of the invention with one or more excipients. In general, the pharmaceutical compositions are prepared by uniformly and intimately bringing into association the compound of the invention with the excipient(s), and then, if necessary, shaping the resulting composition into e.g. a tablet.

The compound of the invention will normally be administered by any conventional administration route, such as the oral or any parenteral route, in the form of a pharmaceutical composition comprising the compound of the invention, optionally in the form of a pharmaceutically acceptable salt, in a pharmaceutically acceptable dosage form. Depending upon the disorder and patient to be treated, as well as the route of administration, the pharmaceutical composition may be administered at varying doses and/or frequencies.

The pharmaceutical compositions must be stable under the conditions of manufacture and storage; thus, if necessary, they should be preserved against the contaminating action of microorganisms such as bacteria and fungi. In case of liquid formulations such as solutions, dispersion, emulsions, and suspensions, the excipient(s) can be a solvent or dispersion medium such as but not limited to water, ethanol, polyol (e.g.

glycerol, propylene glycol and liquid polyethylene glycol), vegetable oils, and suitable mixtures thereof, as well as a solvent or dispersion medium comprising water, ethanol, polyol (e.g. glycerol, propylene glycol and liquid polyethylene glycol), and vegetable oils.

For example, the compound of the invention may be administered orally, buccally or sublingually in the form of tablets, capsules, films, ovules, elixirs, solutions, emulsions, or suspensions, which may contain flavouring or colouring agents.

Pharmaceutical compositions of the present invention suitable for oral administration may be presented as discrete units such as capsules, cachets or tablets, each containing a predetermined amount of the compound of the invention; as multiple units e.g. in the form of a tablet or capsule; as a powder or granules; as a solution or a suspension in an aqueous liquid or a non-aqueous liquid; or as an oil-in-water liquid emulsion or a water-in-oil liquid emulsion. The pharmaceutical compositions may also be presented as a bolus, electuary, or paste.

Solutions or suspensions of the compound of the invention suitable for oral administration may also contain one or more solvents including water, alcohol, polyol, etc., as well as one or more excipients such as pH-adjusting agents, stabilizing agents, surfactants, solubilizers, dispersing agents, preservatives, flavours, etc. Specific examples include N,N-dimethylacetamide, polysorbate 80, polyethylene glycol, and Phosal 50 PG (which consists of phosphatidylcholine, soya-fatty acids, ethanol, mono/diglycerides, propylene glycol and ascorbyl palmitate). The pharmaceutical compositions of the present invention may also be in the form of emulsions, wherein a compound according to Formula (I) may be presented in an emulsion such as an oil-in-water emulsion or a water-in-oil emulsion. The oil may be a natural or synthetic oil or any oil-like substance such as e.g. soy bean oil or safflower oil or combinations thereof.

Tablets may contain excipients such as microcrystalline cellulose, lactose (e.g. lactose monohydrate or anhydrous lactose), sodium citrate, calcium carbonate, dibasic calcium phosphate and glycine, butylated hydroxytoluene (E321), crospovidone, hypromellose, disintegrants such as starch (preferably corn, potato or tapioca starch), sodium starch glycollate, croscarmellose sodium, and certain complex silicates, and granulation binders such as polyvinylpyrrolidone, hydroxypropylmethylcellulose (HPMC), hydroxypropylcellulose (HPC), macrogol 8000, sucrose, gelatin, and acacia. Additionally, lubricating agents such as magnesium stearate, stearic acid, glyceryl behenate, and talc may be included.

A tablet may be made by compression or moulding of a compound of the invention, optionally with one or more excipients. Compressed tablets may be prepared by compressing in a suitable machine the compound of the invention in a free-flowing form such as a powder or granules, optionally mixed with a binder (e.g. povidone, gelatin, hydroxypropylmethyl cellulose), lubricant, inert diluent, preservative, disintegrant (e.g. sodium starch glycolate, cross-linked povidone, cross-linked sodium carboxymethyl cellulose), surface-active agent, and/or dispersing agent. Moulded tablets may be made by moulding in a suitable machine a mixture of the powdered compound of the invention moistened with an inert liquid diluent. The tablets may optionally be coated or scored and may be further treated of processed to provide slow or controlled release of the compound of the invention contained therein using, for example, hydroxypropylmethylcellulose in varying proportions to provide desired release profile.

Solid pharmaceutical compositions of a similar type may also be employed as fillers in gelatin capsules. Preferred excipients in this regard include lactose, starch, cellulose, milk sugar, and high molecular weight polyethylene glycols. For aqueous suspensions and/or elixirs, the compound of the invention may be combined with various sweetening or flavouring agents, colouring matter or dyes, with emulsifying and/or suspending agents, and with diluents such as water, ethanol, propylene glycol and glycerin, and combinations thereof.

Pharmaceutical compositions of the invention suitable for topical administration in the oral cavity include lozenges comprising the compound of the invention in a flavoured basis, usually sucrose and acacia or tragacanth; pastilles comprising the compound of the invention in an inert basis such as gelatin and glycerin, or sucrose and acacia; and mouth-washes comprising the compound of the invention in a suitable liquid carrier.

Pharmaceutical compositions of the invention adapted for topical administration may be prepared as ointments, creams, suspensions, lotions, powders, solutions, pastes, gels, impregnated dressings, sprays, aerosols or oils, transdermal devices, dusting powders, and the like. Such compositions may be prepared via conventional methods containing a compound of the invention. Thus, they may also comprise compatible excipients, such as preservatives, solvents to assist drug penetration, emollient in creams or ointments, and ethanol or oleyl alcohol in lotions. Excipients may constitute from about 1% w/w to about 98% w/w of the composition. Preferably, excipients constitute up to about 80% w/w of the composition. As an illustration only, a cream or ointment is prepared by mixing sufficient quantities of hydrophilic material and water, containing from about 5-10% w/w of the compound, in sufficient quantities to produce a cream or ointment having the desired consistency.

Pharmaceutical compositions of the invention adapted for transdermal administration may be presented as discrete patches intended to remain in intimate contact with the epidermis of the recipient for a prolonged period of time. For example, the compound of the invention may be delivered from the patch by iontophoresis.

For applications to external tissues, for example the mouth and skin, the pharmaceutical compositions of the invention are preferably applied as a topical ointment or cream. When formulated in an ointment, the compound of the invention may be employed with either a paraffinic or a water-miscible ointment base.

Alternatively, the compound of the invention may be formulated in a cream with an oil-in-water cream base or a water-in-oil base.

For parenteral administration, fluid unit dosage forms are prepared comprising the compound of the invention and a sterile vehicle, such as but not limited to water, alcohols, polyols, glycerine, and vegetable oils, with water being preferred. The compound of the invention, depending on the vehicle and concentration used, can be either colloidal, suspended, or dissolved in the vehicle. In preparing solutions, the compound of the invention can be dissolved in water for injection and filter sterilised before filling into a suitable vial or ampoule and sealing.

Advantageously, agents such as local anaesthetics, preservatives, and buffering agents can be dissolved in the vehicle. To enhance the stability, the pharmaceutical composition can be frozen after filling into the vial, and the water may then be removed under vacuum. The dry lyophilized powder is then sealed in the vial and an accompanying vial of water for injection may be supplied to reconstitute the liquid prior to use.

Pharmaceutical compositions of the present invention suitable for injectable use include sterile aqueous solutions or dispersions. Furthermore, such pharmaceutical compositions can be in the form of sterile powders for the extemporaneous preparation of such sterile injectable solutions or dispersions. In all cases, the final injectable form must be sterile and must be effectively fluid for easy syringability.

Parenteral suspensions are prepared in substantially the same manner as solutions, except that the compound of the invention is suspended in the vehicle instead of being dissolved, and sterilization cannot be accomplished by filtration. The compound of the invention can be sterilised by exposure to ethylene oxide before suspending in the sterile vehicle. Advantageously, a surfactant or wetting agent is included in the pharmaceutical composition to facilitate uniform distribution of the compound of the invention.

It should be understood that in addition to the ingredients particularly mentioned above, the pharmaceutical compositions of the present invention may include other agents conventional in the art having regard to the type of formulation in question. For example, those pharmaceutical compositions suitable for oral administration may include flavouring agents. A person skilled in the art will know how to choose a suitable formulation and how to prepare it, e.g. with guidance from Remington's Pharmaceutical Sciences, $18^{th}$ edition, Mack Publishing Company, 1990, or a newer edition. A person skilled in the art will also know how to choose a suitable administration route and dosage.

It will be recognized by a person skilled in the art that the optimal quantity and spacing of individual dosages of the compound of the invention will be determined by the nature and extent of the condition being treated, the form, route and site of administration, and the age and condition of the particular subject being treated, and that a physician will ultimately determine appropriate dosages to be used. This dosage may be repeated as often as appropriate. If side effects develop, the amount and/or frequency of the dosage can be altered or reduced, in accordance with normal clinical practice.

All % values mentioned herein are % w/w unless the context requires otherwise.

Definitions

The articles "a", "an", and "the" are used herein to refer to one or to more than one (i.e. at least one) of the grammatical objects of the article. By way of example "an analogue" means one analogue or more than one analogue.

As used herein the term "compound(s) of the invention" are used interchangeably and refer to compounds of formula (I).

As used herein the term "direct antibacterial effect" refers to the antibacterial activity of erythromycin and analogues which occurs through binding to the bacterial rRNA complex. This effect does not require presence of any host immune system components and therefore is apparent in standard antibacterial assays such as in vitro Minimum Inhibitory Concentration (MIC) assays and disk inhibition assays.

As used herein the term "without substantial antibacterial activity" is intended to mean that the compound of the invention has a MIC value of >64 µg/ml when tested in accordance with Example 2 herein for its antibacterial activity in E. coli, S. salivarius, L. casei and B. longum.

The pharmaceutically acceptable salts of the compound of the invention include conventional salts formed from pharmaceutically acceptable inorganic or organic acids or bases as well as quaternary ammonium acid addition salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts.

LEGENDS TO FIGURES

Figure 1:
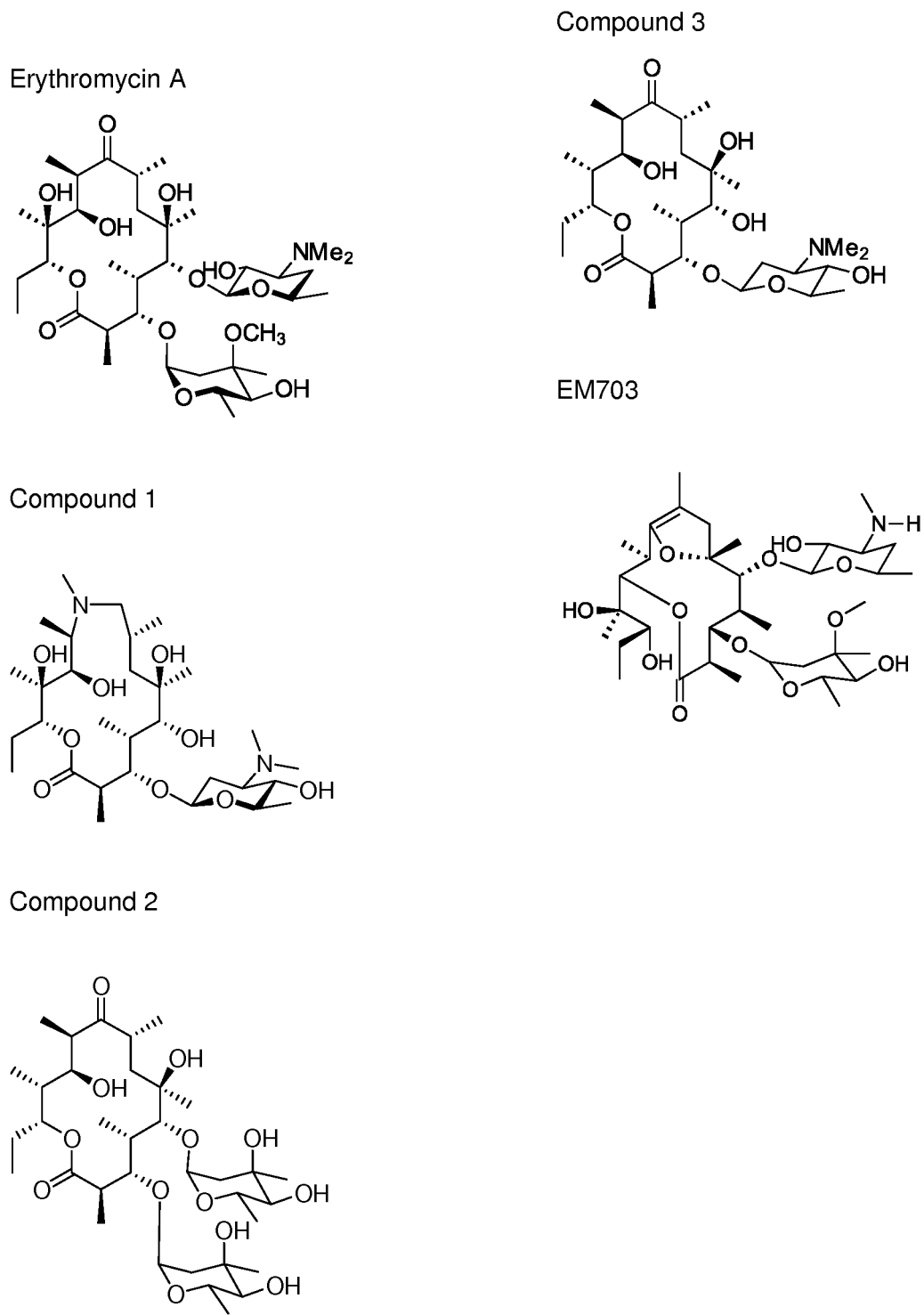
Figure 2:
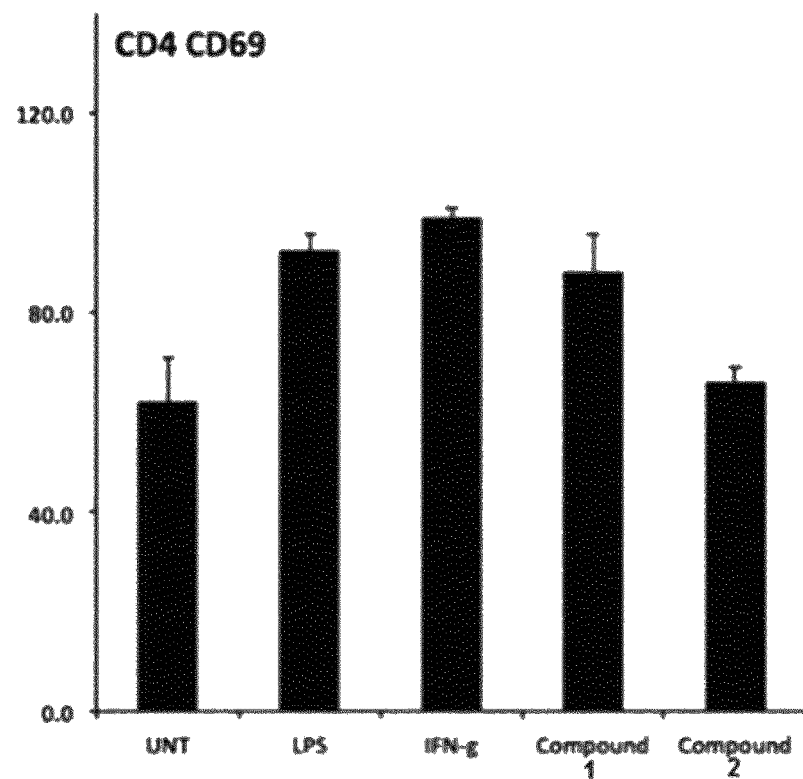
Figure 2:
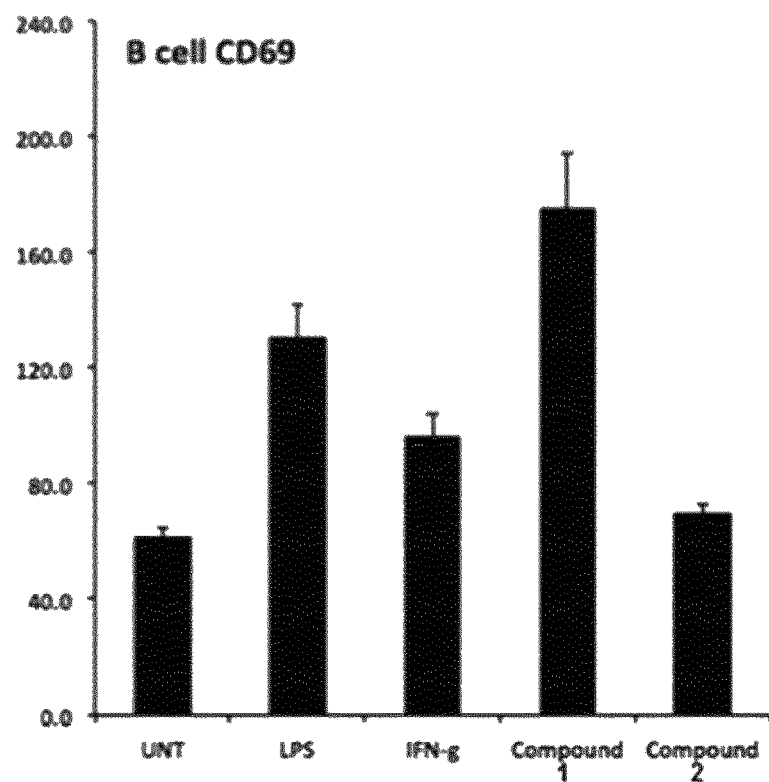

FIG. 1. The structures of the macrolides Erythromycin A, Compound 1, Compound 2, compound 3 and EM703.

FIG. 2. CD69 upregulation on T- and B-cells. PBMC were treated for 24 h with compound 1, compound 2 and activation controls LPS and IFN-gamma. The expression of the early activation marker CD69 was measured on the CD4+ T cell population (left) and CD19+ B cell population (right) with flow cytometry. Values represents mean fluorescent intensity, MFI, and error bars standard deviation in the triplicate samples.

Figure 3:
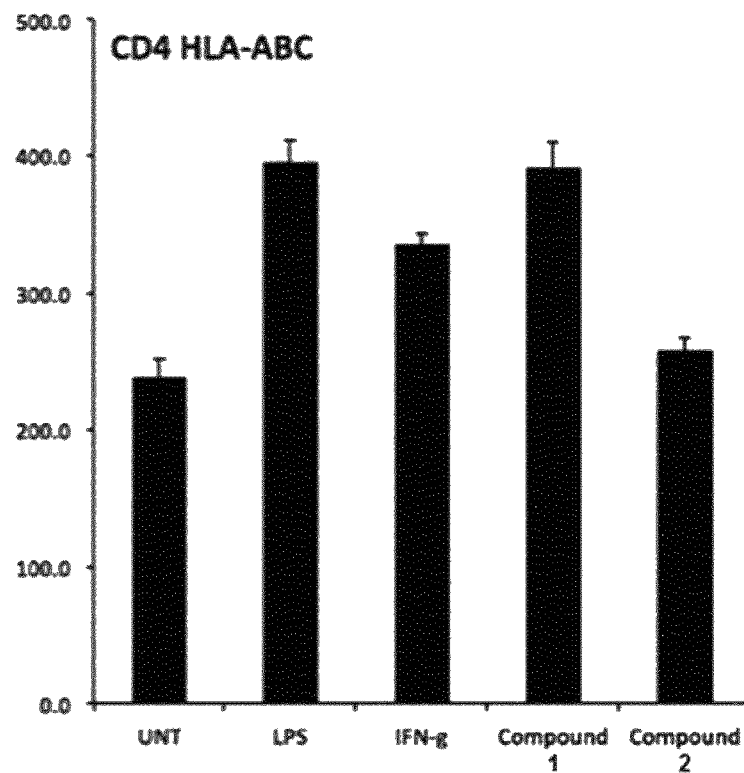
Figure 3:
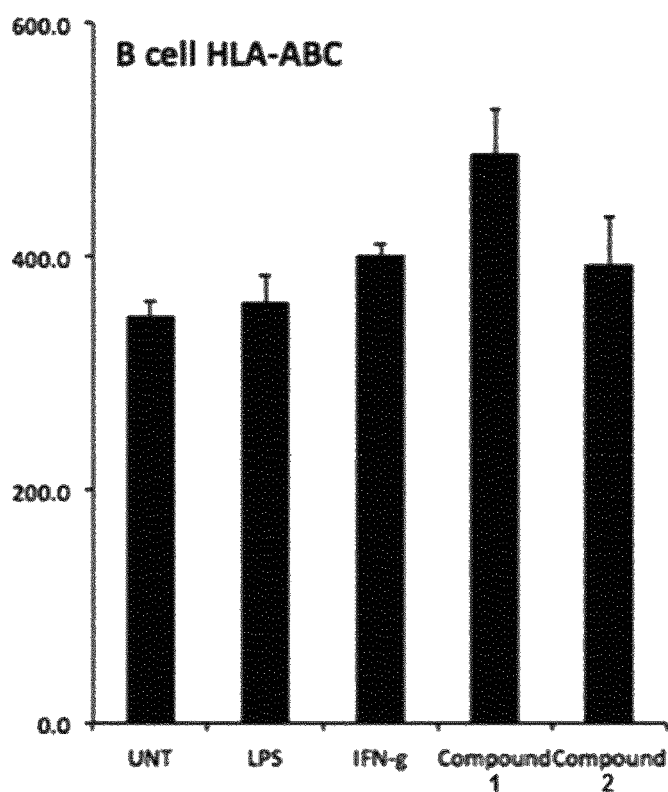

FIG. 3. HLA-A,B,C upregulation on T- and B-cells. PBMC were treated for 24 h with compounds 1 or 2 and activation controls LPS and IFN-γ. The expression of HLA-A,B,C was measured on the CD4+ T cell population (left) and CD19+ B cell population (right) with flow cytometry. Values represents mean fluorescent intensity, MFI, and error bars standard deviation in the triplicate samples.

FIG. 4. CD80 and HLA-DR upregulation on blood monocytes. PBMC were treated for 24 h with compounds 1 or 2 as well as activation controls LPS and IFN-gamma. The expression of CD80 and HLA-DR was measured on the monocyte cell population with flow cytometry. Values represents mean fluorescent intensity, MFI, and error bars standard deviation in the triplicate samples.

FIG. 5. CD80 upregulation on blood monocytes. PBMC were treated for 24 h with compounds 1 or 2 as well as activation control IFN-gamma. The expression of CD80 was measured on the monocyte cell population with flow cytometry. Values represents mean fluorescent intensity, MFI, and error bars standard deviation in the triplicate samples.

FIG. 6. Production of IL-10 from PBMCs after stimulation with compound 1 for 48 h or 1 week, measured with ELISA.

FIG. 7. CD4 T cell proliferation after 6 days stimulation with compound 1, measured with proliferation dye Celltrace violet (Invitrogen) and flow cytometry. Untreated cells (UNT) or compound 2 were used as controls.

FIG. 8. Upregulation of IL-7 receptor a (CD127) on CMV specific CD8 T cells after incubation with compound 1, measured with flow cytometry.

Figure 9:
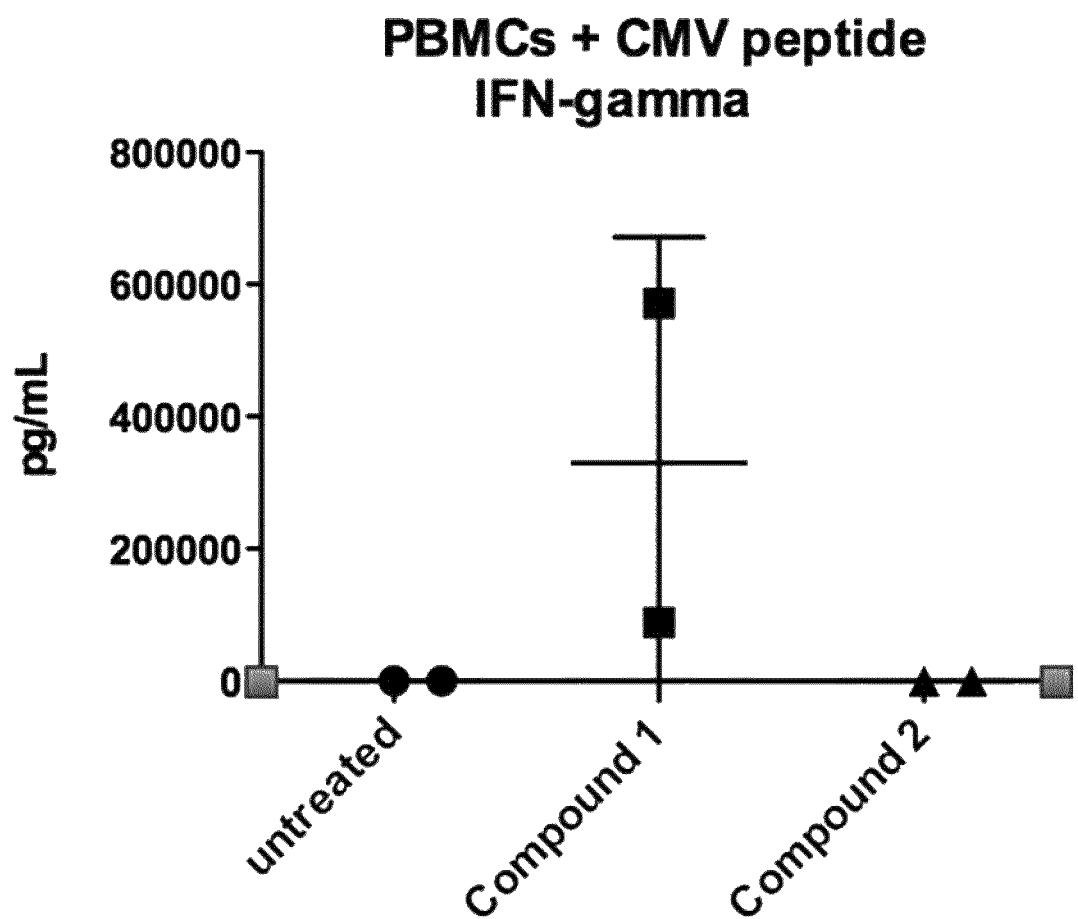

FIG. 9: Interferon-gamma secretion (as measured by cytometric bead assay) from PBMCs (from a CMV+ donor) grown with CMV peptides in the presence or absence of compound 1 or 2 for 5 days.

Figure 10:
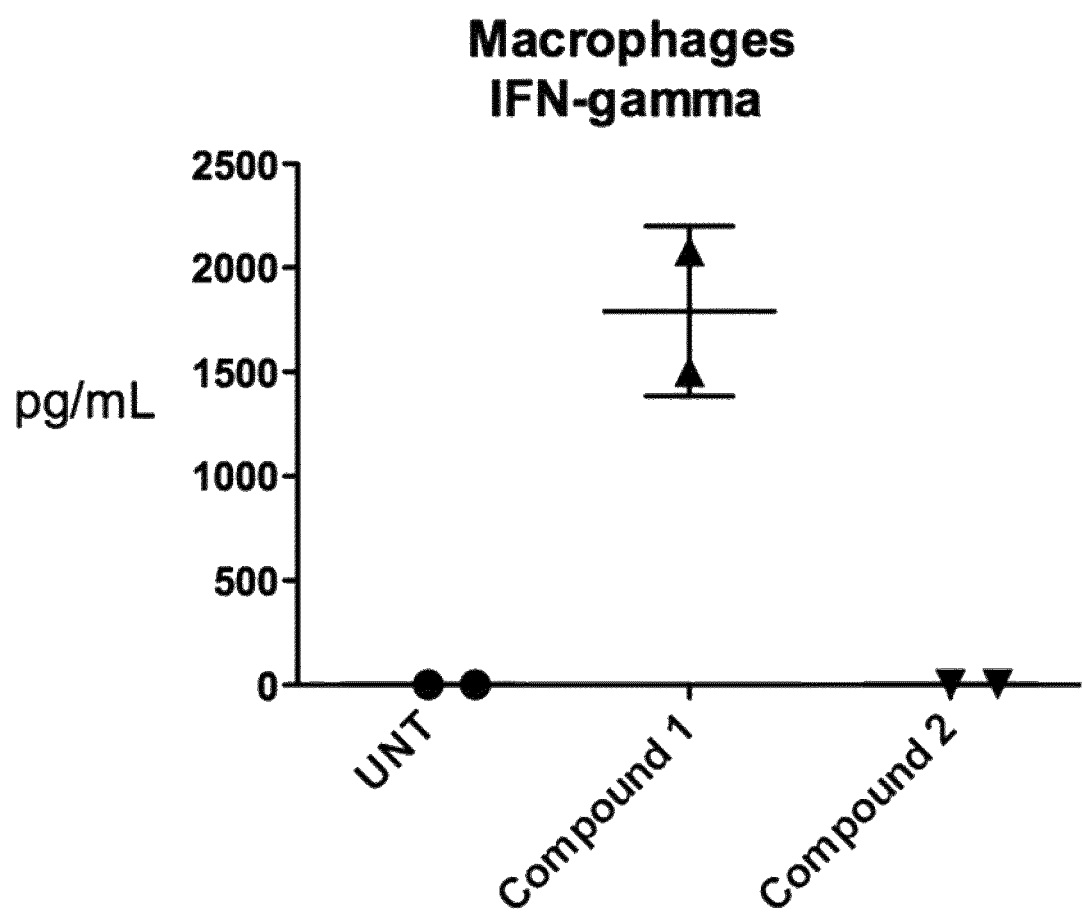

FIG. 10: Interferon-gamma secretion (as measured by cytometric bead assay) from macrophages stimulated with indicated compound for 48 h.

Figure 11:
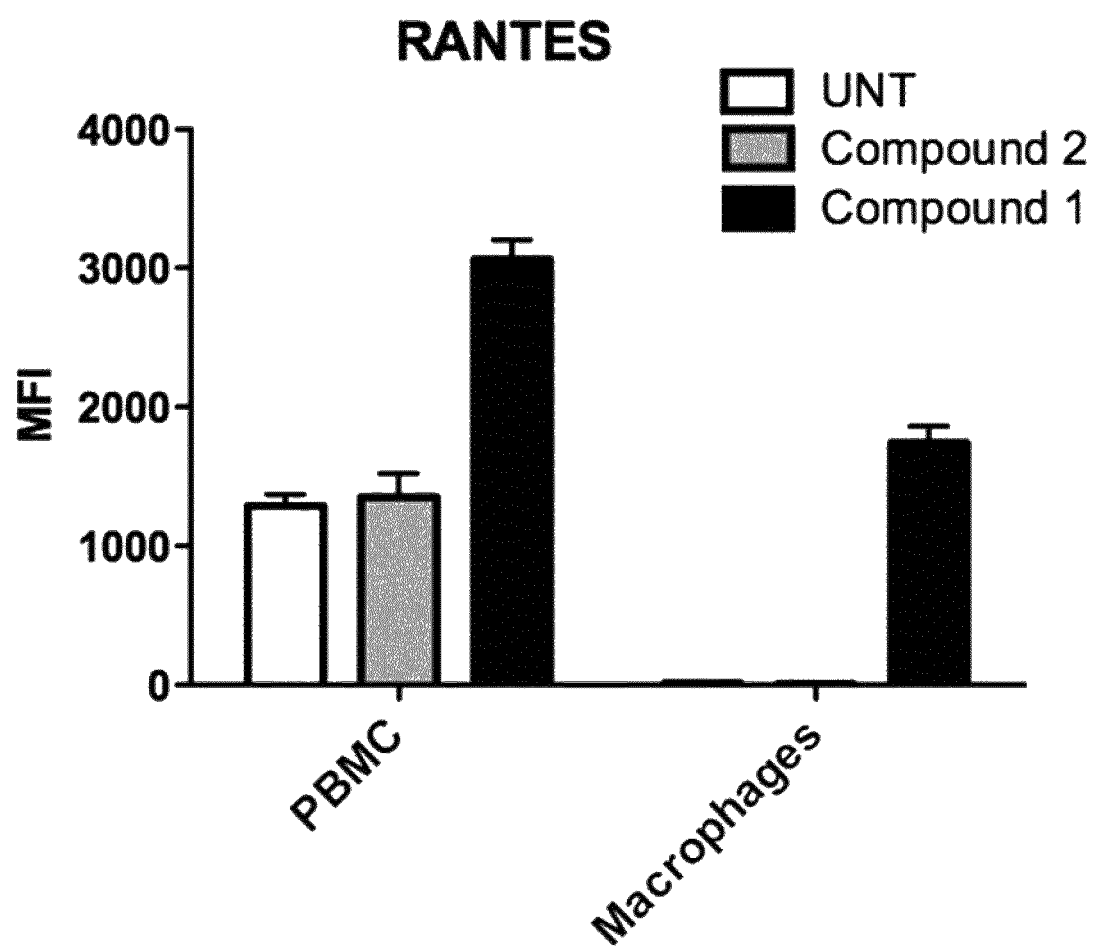

FIG. 11: Chemokine RANTES secretion (as measured by cytometric bead assay) from PBMC or macrophages stimulated with indicated compound for 48 h.

Figure 12:
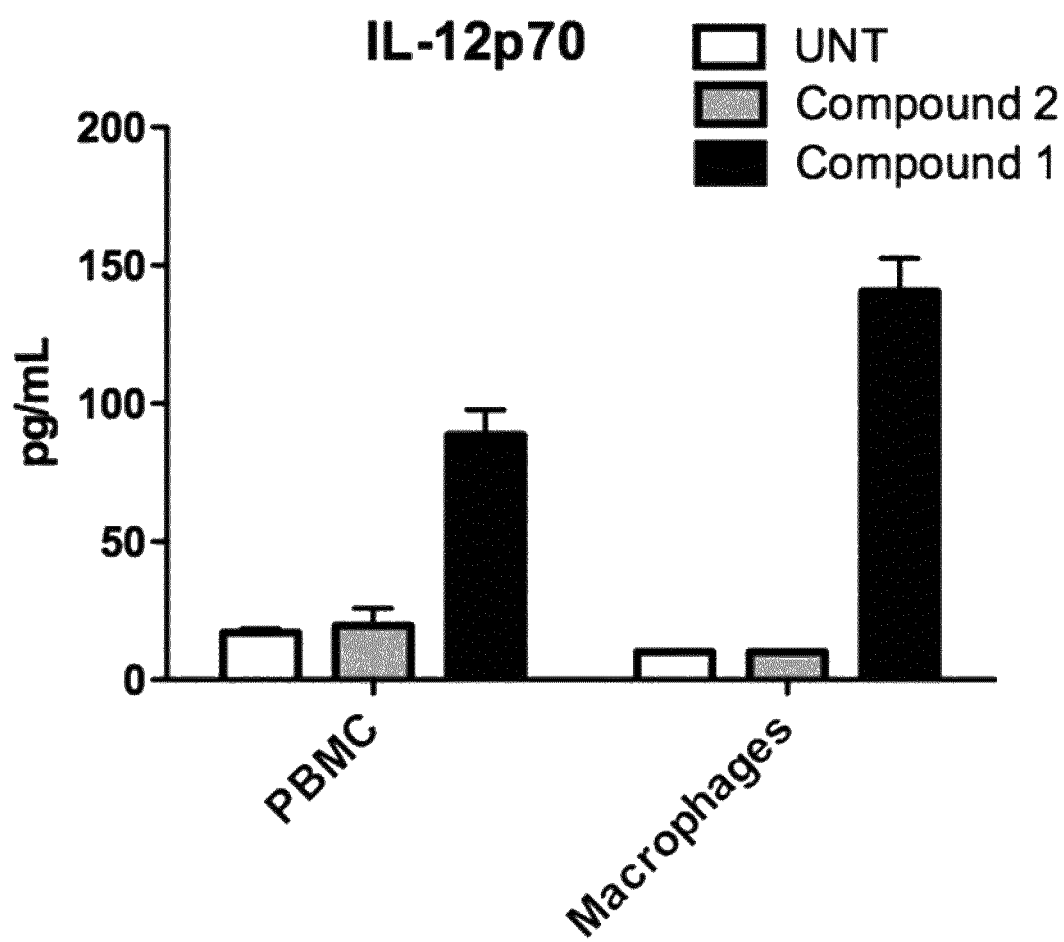

FIG. 12: IL12p70 secretion (as measured by cytometric bead assay) from PBMC or macrophages stimulated with indicated compound for 48 h.

Figure 13:
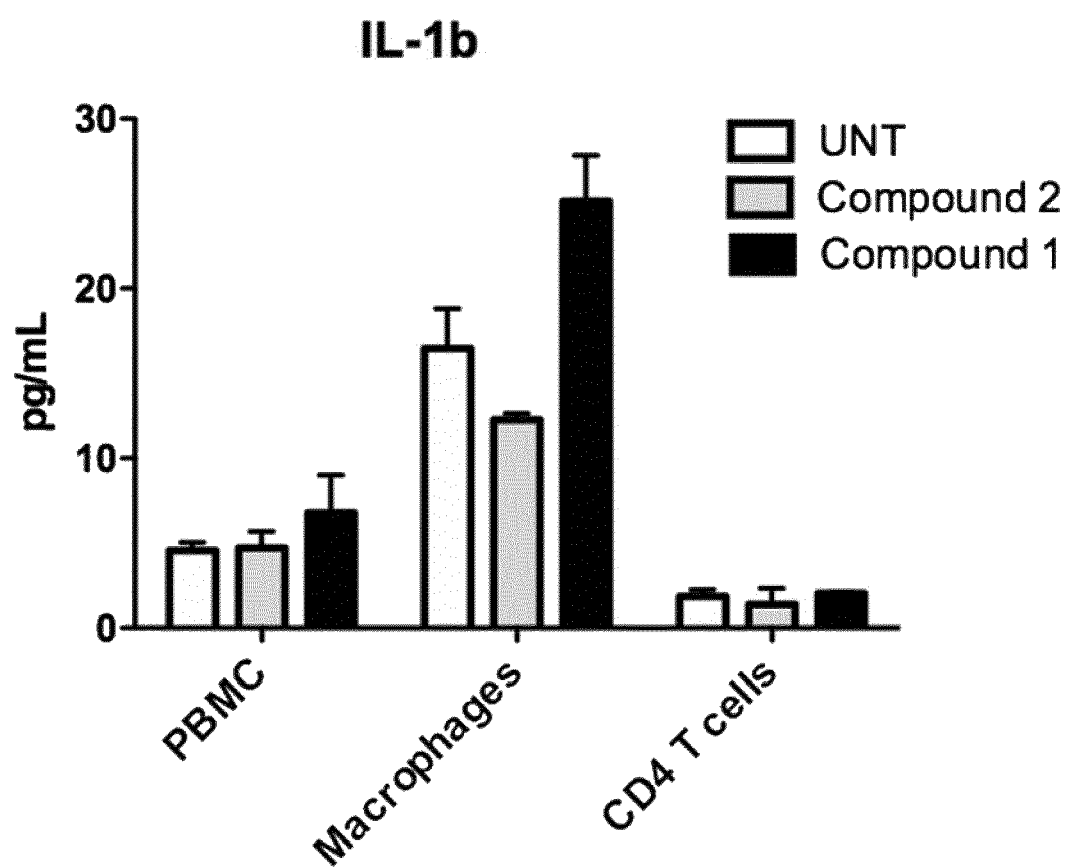

FIG. 13: IL1b secretion (as measured by cytometric bead assay) from PBMC, macro-phages or CD4 T cells stimulated with indicated compound for 48 h.

Figure 14:
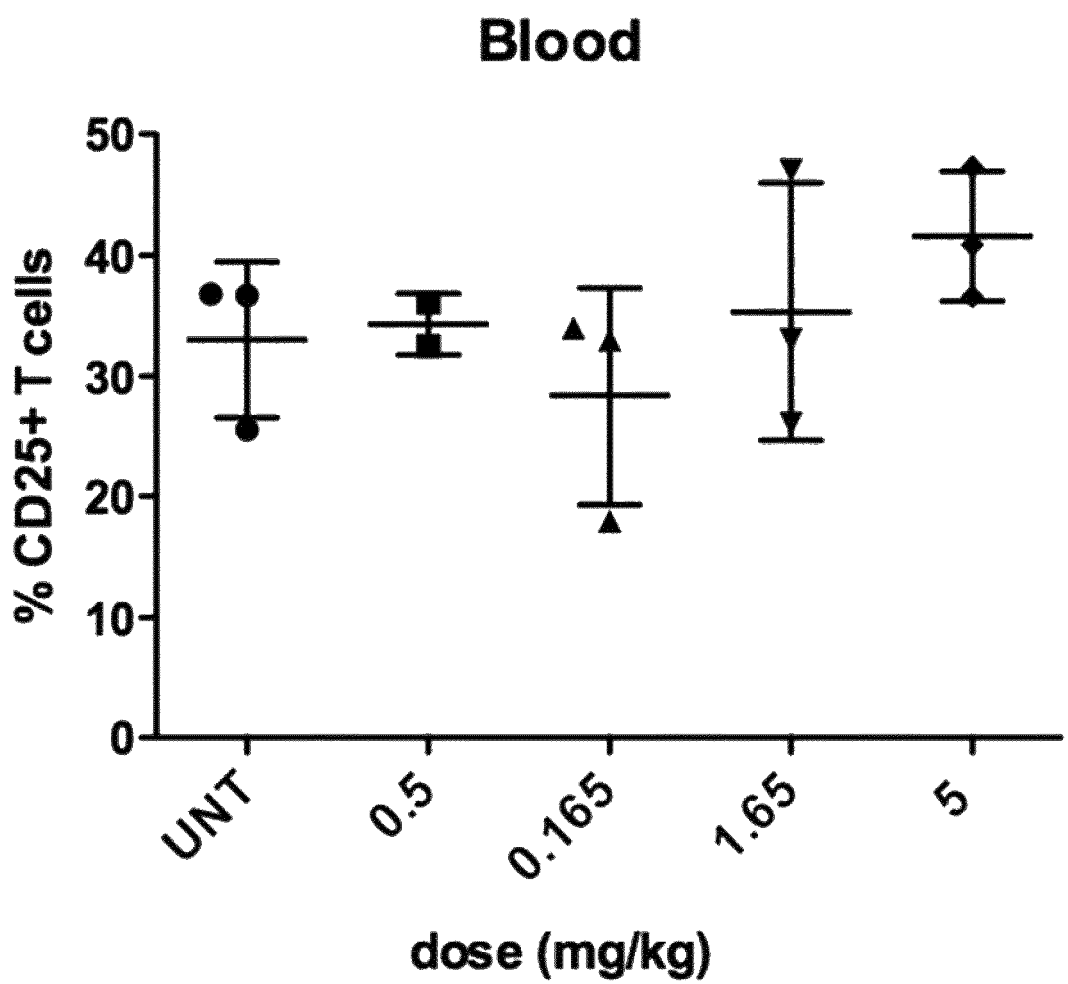

FIG. 14: % CD25 high cells in blood of C57bl/6 mice injected 24 h previously with indicated dose of compound 1. CD25 expression was measured by flow cytometry.

Figure 15:
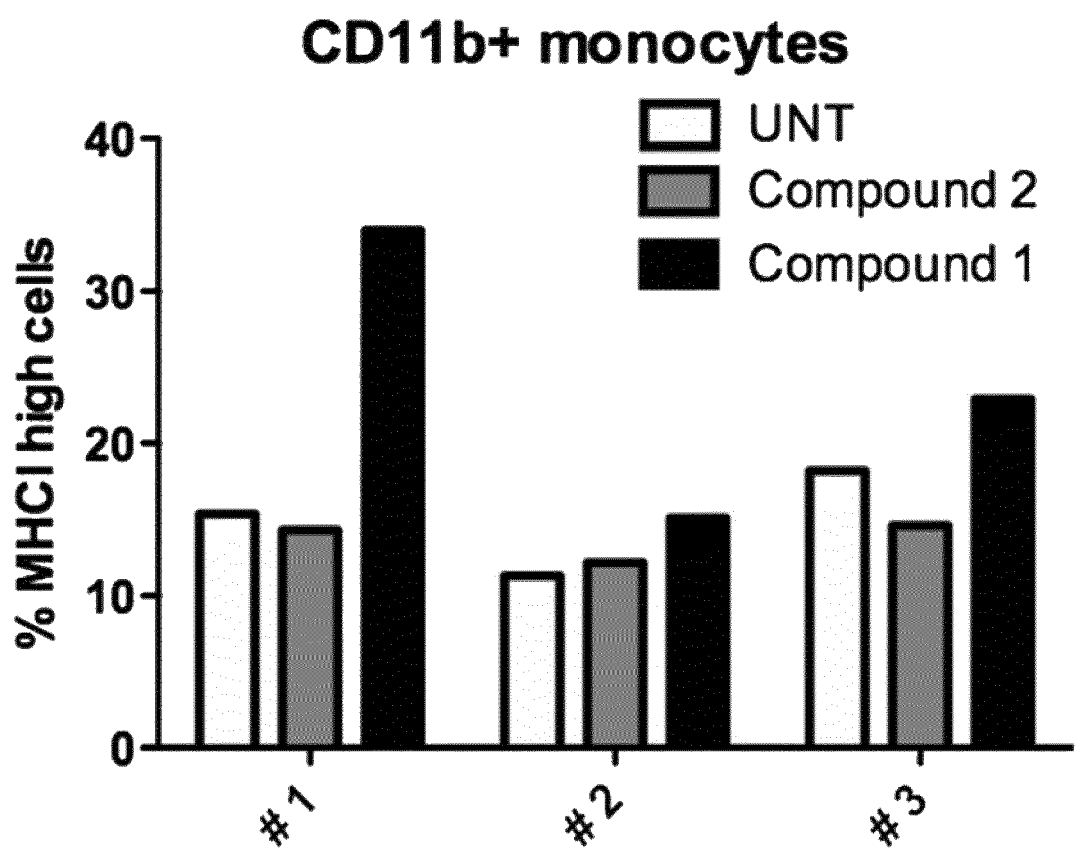

FIG. 15: % MHC class I high CD11b+ cells in spleen of 3 individual C57bl/6 mice injected 24 h previously with indicated compound. MHC class I and CD11b expression was measured by flow cytometry.

EXPERIMENTAL

Materials

Unless otherwise indicated, all reagents used in the examples below are obtained from commercial sources.

Antibodies

Anti-CD80 V450, anti-CD69 PE, anti HLA-DR APC-R700, anti CD127-APC, and anti-Anti-HLA-A,B,C FITC were purchased from BD Biosciences. Celltrace violet for T cell proliferation assay was purchased from Invitrogen. ELISA antibodies were purchased from BD Biosciences.

Media

RPMI-1640 (Invitrogen) supplemented with 25 mM HEPES, L-glutamine, Sodium pyruvate, 10% fetal bovine serum (Gibco), 100 μg/mL penicillin and 100 μg/mL streptomycin.

General Biology Methods

The effect of the compounds of the invention on immune stimulation may be tested using one or more of the methods described below:

General Compound Methods

Compound Analysis—Solubility and Stability in Solution

Analysis of Fermentation Broths and Compounds

An aliquot of fermentation broth obtained as described below was shaken vigorously for 30 minutes with an equal volume of ethyl acetate, and then separated by centrifugation, or the already isolated compounds were dissolved in methanol:water (9:1, 0.1 mg/ml), and then separated by centrifugation. Supernatants were analysed by LC-MS and LC-MS/MS and chromatography was achieved over base-deactivated Luna C18 reversed-phase silica (5 micron particle size) using a Luna HPLC column (250×4.6 mm; Phenomenex (Macclesfield, UK)) heated at 40° C. Agilent 1100 HPLC system comprising of quaternary pump, auto sampler, column oven and diode array detector coupled to a Bruker Esquire ion trap MS.

Mobile phase A=0.1% formic acid in water

Mobile phase B=0.1% formic acid in acetonitrile

Gradient: T=0 min, B=50%; T=4.5 min, B=50%; T=7 min, B=100%; T=10.5 min, B=100%; T=10.75 min, B=50%; T=13 min, B=50%.

Compounds were identified by LC-MS and LC-MS/MS and quantified by LC-MS/MS against an internal standard.

Analysis of Marker Expression by Flow Cytometry

Human peripheral blood mononuclear cells (PBMCs) were purified from healthy donors with Ficoll-Paque density centrifugation. Cells were cultured in complete RPMI-1640 media (Invitrogen) supplemented with 25 mM HEPES, L-glutamine, Sodium pyruvate (Sigma), 10% fetal bovine serum, 100 μg/mL penicillin and 100 μg/mL streptomycin (Hyclone) for 24-72 hours in 37° C., 5% $CO_2$ and stimulated with and increasing concentrations of compound 1 and 2. Cells were then washed in PBS and stained with monoclonal antibodies specific for cell surface markers (BD Pharmingen) and analysed with flow cytomtery using a BD FACS Canto II flow cytometer. All samples were tested in duplicates.

Cytomegalovirus (CMV) Cultures

Human peripheral blood mononuclear cells (PBMCs) were purified from healthy CMV positive donors with Ficoll-Paque density centrifugation. The PBMC were labeled with 5 μM celltrace violet (Invitrogen) in PBS for 15 minutes and then washed with complete cell culture medium. The labeled PBMC was cultured in the presence of a peptide library spanning the CMV pp65 protein (1 μg peptide/ml, JPT) in AIM-V media (Invitrogen) supplemented with L-glutamine, Sodium pyruvate (Sigma), 10% fetal bovine serum, 100 μg/mL penicillin and 100 μg/mL streptomycin (Hyclone) for 6-8 days in 37° C., 5% $CO_2$. Cell proliferation was assessed with flow cytomtery using a BD FACS Canto II flow cytometer.

ELISA

Supernatant IL-10 was measured with a standard sandwich ELISA (all antibodies from BD Biosciences) after 48 hours and 7 days incubation with 2.5 µM of compound 1 and 100 U/mL IL-2 (Miltenyi Biotechnologies) in complete RPMI media, 37° C., 5% $CO_2$ TLR2 Assay Samples and controls were tested in duplicate on recombinant HEK-293-TLR cell lines using a cell reporter assay at Invivogen using their standard assay conditions. These cell lines functionally over-express human TLR2 protein as well as a reporter gene which is a secreted alkaline phosphatase (SEAP). The production of this reporter gene is driven by an NFkB inducible promoter. The TLR reporter cell lines activation results are given as optical density values, as compared to negative controls (OD). 20 µl of each test article were used to stimulate the hTLR2 reporter cell lines in a 200 µl of final reaction volume. Samples were tested in duplicate, with at least two concentrations tested –20 µM and 10 µM.

Assessment of Cell Permeability (Bidirectional)

10 µM Test article was added to the apical (A) surface of Caco-2 cell monolayers (in HBSS buffer with 0.3% DMSO and 5 µM LY at 37 degrees C.) and compound permeation into the basolateral (B) compartment measured following 90 minutes incubation. This was also performed in the reverse direction (basolateral to apical) to investigate active transport. LC-MS/MS is used to quantify levels of both the test and standard control compounds. Efflux ratio was calculated by dividing the B to A permeability by the B to A permeability.

Drug permeability: Papp=(VA/(Area×time))×([drug] accepter /(([drug]initial, donor) ×Dilution Factor)

Assessment of Metabolic Stability (Microsome Stability Assay)

Rate of metabolism in microsomes was tested as follows:

Human liver microsomes were diluted with buffer C (0.1 M Potassium Phosphate buffer, 1.0 mM EDTA, pH 7.4) to a concentration of 2.5 mg/mL. Microsomal stability studies were carried out by adding 30 µL of 1.5 µM compound spiking solution to wells (1.5 µL of 500 µM spiking solution (10 µL of 10 mM DMSO stock solution into 190 µL ACN to eventually generate final test concentration of 1 uM) and 18.75 µL of 20 mg/mL liver microsomes into 479.75 µL of Buffer C). All samples were pre-incubated for approximately 15 minutes at 37° C. Following this, the reaction was initiated by adding 15 µL of the NADPH solution (6 mM) with gentle mixing. Aliquots (40 µL) were removed at 0, 5, 15, 30 and 45 minutes and quenched with ACN containing internal standard (135 µL). Protein was removed by centrifugation (4000 rpm, 15 min) and the sample plate analysed for compound concentration by LC-MS/MS. Half-lives were then calculated by standard methods, comparing the concentration of analyte with the amount originally present.

EXAMPLES

Example 1—Generation of Compound 1

Generation of az-AG

Azithromycin aglycone was generated using methods described in the literature (Djokic, S., et al., 1988). In brief azithromycin is converted to azithromycin aglycone by the acidic removal of the 3-O and 5-O sugars. The 5-O amino sugar is first oxidised and pyrolyzed to facilitate cleavage.

Generation of Biotransformation Strains Capable of Glycosylating Erythromycin Aglycones (Erythronolides)

Generation of S. erythraea 18A1 (pAES52)

pAES52, an expression plasmid containing angAI, angAII, angCVI, ang-orf14, angMIII, angB, angMI and angMII along with the actII-ORF4 pactI/III expression system (Rowe et al., 1998) was generated as follows.

The angolamycin sugar biosynthetic genes were amplified from a cosmid library of strain S. eurythermus ATCC23956 obtained from the American Type Culture Collection (Manassas, Va., USA). The biosynthetic gene cluster sequence was deposited as EU038272, EU220288 and EU232693 (Schell et al. 2008).

The biosynthetic gene cassette was assembled in the vector pSG144 as described previously (Schell et al. 2008, ESI), adding sequential genes until the 8 required for sugar biosynthesis were obtained, creating plasmid pAES52.

pAES52 was transformed into strain 18A1 (WO2005054265).

Transformation of pAES52 into S. erythraea 18A1 pAES52 was transformed by protoplast into S. erythraea 18A1 using standard methods (Kieser et al 2000, Gaisser et al. 1997). The resulting strain was designated ISOM-4522, which is deposited at the NCIMB on 24 Jan. 2017 with Accession number: NCIMB 42718.

Generation of S. erythraea SGT2 (pAES54)

pAES54, an expression plasmid containing angAI, angAII, angCVI, ang-orf14, angMIII, angB, angMI and angMII along with the actII-ORF4 pactI/III expression system (Rowe et al. 1998) was generated as follows The angolamycin sugar biosynthetic genes were amplified from a cosmid library of strain S. eurythermus ATCC23956 obtained from the American Type Culture Collection (Manassas, Va., USA). The biosynthetic gene cluster sequence was deposited as EU038272, EU220288 and EU232693 (Schell et al. 2008).

The biosynthetic gene cassette was assembled in the vector pSG144 as described previously (Schell et al. 2008, ESI), adding sequential genes until the 8 required for sugar biosynthesis were obtained, creating plasmid pAES52.

Plasmid pAES54 was made by ligating the 11,541 bp SpeI-NheI fragment containing the actII-ORF4 pactI/III promotor system and the 8 ang genes was excised from pAES52 with the 5,087 bp XbaI-SpeI fragment from pGP9, containing an apramycin resistance gene, oriC, oriT for transfer in streptomycetes and phiBT1 integrase with attP site for integrative transformation. (The compatible NheI and XbaI sites were eliminated during the ligation.)

pAES54 was then transformed into S. erythraea SGT2 (Gaisser et al. 2000, WO2005054265).

Transformation of pAES54 into S. erythraea SGT2 pAES54 was transferred by conjugation into S. erythraea SGT2 using standard methods. In brief, E. coli ET12567 pUZ8002 was transformed with pAES54 via standard procedures and spread onto 2TY with Apramycin (50 µg/mL), Kanamycin (50 µg/mL), and Chloramphenicol (33 µg/mL) selection. This plate was incubated at 37° C. overnight. Colonies from this were used to set up fresh liquid 2TY cultures which were incubated at 37° C. until late log phase was reached. Cells were harvested, washed, mixed with spores of S. erythraea SGT2, spread onto plates of R6 and incubated at 28° C. After 24 hours, these plates were overlaid with 1 mL of sterile water containing 3 mg apramycin and 2.5 mg nalidixic acid and incubated at 28° C. for a further 5-7 days. Exconjugants on this plate were transferred to fresh plates of R6 containing apramycin (100 µg/mL).

Alternative biotransformation Strain

Alternatively, BIOT-2945 (Schell et al. 2008) may be used as the biotransformation strain, as this also adds angolosamine to erythronolides.

Biotransformation of *Azithromycin aglycone*

Erlenmeyer flasks (250 mL) containing SV2 medium (40 mL) and 8 uL thiostrepton (25 mg/mL) were inoculated with 0.2 mL of spore stock of strain ISOM-4522 and incubated at 30° C. and shaken at 300 rpm with a 2.5 cm throw for 48 hours.

SV2 Media:

| Ingredient | Amount |
| --- | --- |
| glycerol | 15 g |
| glucose | 15 g |
| soy peptone A3SC | 15 g |
| NaCl | 3 g |
| CaCO$_3$ | 1 g |
| RO water | To final volume of 1 L |

Pre-sterilisation pH adjusted to pH 7.0 with 10M HCl
Sterilised by autoclaving @ 121° C., 30 minutes Sterile bunged falcon tubes (50 mL) containing EryPP medium (7 mL) were prepared and inoculated with culture from seed flask (0.5 mL per falcon tube) without antibiotics. The falcons were incubated at 30° C. and shaken at 300 rpm with a 2.5 cm throw for 24 hours.

ERYPP Medium:

| Ingredient | Amount |
| --- | --- |
| toasted soy flour (Nutrisoy) | 30 g |
| glucose | 50 g |
| (NH$_4$)$_2$SO$_4$ | 3 g |
| NaCl | 5 g |
| CaCO$_3$ | 6 g |
| RO water | To final volume of 1 L |

Pre-sterilisation pH adjusted to pH 7.0 with 10M HCl
Sterilised in situ by autoclaving @ 121° C., 30 minutes
Post sterilisation 10 ml/L propan-1-ol added After 24 hours, azithromycin aglycone (0.5 mM in DMSO, 50 uL) was added to each falcon tube and incubation continued at 300 rpm with a 2.5 cm throw for a further 6 days.

Isolation of Compound 1

Whole broth was adjusted to pH 9.5 and extracted twice with one volume of ethyl acetate. The organic layers were collected by aspiration following centrifugation (3,500 rpm, 25 minutes). The organic layers were combined and reduced in vacuo to reveal a brown gum that contained compound 1. This extract was partitioned between ethyl acetate (200 ml) and aqueous ammonium chloride (20 ml of a 50% concentrated solution). After separation, the organic layer was extracted with a further volume (200 ml) of the ammonium chloride aqueous solution. The combined aqueous layers were then adjusted to pH 9.0 with aqueous sodium hydroxide and then extracted twice with one volume equivalent of ethyl acetate. The organic layers were combined and reduced in vacuo to a brown solid. This extract was then applied to a silica column and eluted step wise (in 500 ml lots) with:

| Solvent | Hexanes | EtOAc | MeOH | Aq. NH$_4$OH |
| --- | --- | --- | --- | --- |
| A | 0.499 | 0.499 | 0 | 0.002 |
| B | 0.250 | 0.748 | 0 | 0.002 |
| C | 0 | 0.998 | 0 | 0.002 |
| D | 0 | 0.988 | 0.01 | 0.002 |
| E | 0 | 0.978 | 0.02 | 0.002 |
| F | 0 | 0.968 | 0.03 | 0.002 |
| G | 0 | 0.958 | 0.04 | 0.002 |

Compound 1 was predominantly in F and G. These solvents were combined and reduced in vacuo to yield a brown solid containing compound 1. This material was then purified by preparative HPLC (C18 Gemini NX column, Phenomenex with 20 mM ammonium acetate and acetonitrile as solvent). Fraction containing the target compound were pooled and taken to dryness followed by desalting on a C18 SPE cartridge.

Example 2—Assessment of Direct Antibacterial Activity

The bioactivity of macrolide compounds against 4 strains of common gut bacteria (*Escherichia coli, Streptococcus salivarius* subsp. *salivarius, Lactobacillus casei* and *Bifidobacterium longum* subsp. *infantis*) and common mammalian skin isolate *Micrococcus luteus*, was assessed using the Minimum Inhibitory Concentration (MIC) assay. Bacterial strains were purchased from DSMZ (Brunswick, Germany) except *M. luteus* which was obtained from NCIMB, and stored in 20% glycerol at −80° C. Stock solutions (100% DMSO) of positive controls (azithromycin and erythromycin), and of test compounds 1 and 2 were diluted in broth to working stock concentrations of 256 µg/ml (final assay testing concentration range 128 µg/ml to 0.00391 µg/ml). Stock solutions of all other compounds were diluted in broth to working stock concentrations of 128 µg/ml (final assay testing concentration range 64 µg/ml to 0.00195 µg/ml). Bacterial strains were cultivated in appropriate broth in an anaerobic chamber at 37° C., except for *M. luteus* which was incubated aerobically at 37° C. 18 h cultures were diluted in broth to an OD595 of 0.1 and then further diluted 1:10. In 96-well plates, in duplicate, 200 µl working stock of test compound was transferred to well 1 and serially diluted (1:2) in broth. 100 µl bacterial suspension was aliquoted into each well and mixed thoroughly. Appropriate sterility controls were included and plates were incubated in an anaerobic chamber, or aerobically (*M. luteus*) at 37° C. for 18 h. The MIC was determined to be the concentration of test compound in the first well with no visible growth.

TABLE 1

| | *Escherichia coli* | *Streptococcus salivarius* | *Lactobacillus casei* | *Bifidobacterium longum* | *Micrococcus luteus* |
| --- | --- | --- | --- | --- | --- |
| Azithromycin | <8 µg/ml | <0.5 µg/ml | <1.0 µg/ml | >64 µg/ml | 0.125 µg/ml |
| Erythromycin | >64 µg/ml | <0.06 µg/ml | <0.25 µg/ml | >64 µg/ml | <0.0625 µg/ml |
| Compound 1 | >64 µg/ml | >64 µg/ml | >64 µg/ml | >64 µg/ml | >256 µg/ml |
| EM703 | | | | | 64-128 µg/ml |

As can be seen from the data presented in Table 1, compound 1 shows no antibacterial activity against any of the bacterial strains tested, whilst erythromycin and azithromycin show potent activity against a number of the strains.

Example 3—Assessment of Immune Stimulatory Activity

Human peripheral blood mononuclear cells (PBMCs) were purified from healthy donors with Ficoll-Paque density centrifugation. Cells were cultured in complete RPMI-1640 medium (Invitrogen) supplemented with 25 mM HEPES, L-glutamine, Sodium pyruvate (Sigma), 10% fetal bovine serum, 100 µg/mL penicillin and 100 µg/mL streptomycin (Hyclone). Cells were stimulated for 24 h (study 1-4) or 48 h to 1 week (study 5) in 37° C., 5% $CO_2$ with increasing concentrations of compound 1 and 2 in tissue culture plates. The cells were removed from the plate, washed in PBS and analysed for expression of cell specific surface markers and MHC class I with flow cytometry using monoclonal antibodies from BD Pharmingen and a FACS Canto II flow cytometer.

Supernatant IL-10 was measured with a standard sandwich ELISA (all antibodies from BD Biosciences) after 48 hours and 7 days incubation with 2.5 uM of compound 1 and 100 U/mL IL-2 (Miltenyi Biotechnologies) in complete RPMI media, 37° C., 5% $CO_2$.

Study1: After 24 h of in vitro stimulation of peripheral blood mononuclear cells (PBMC) with 1 µM compound 1 (FIG. 1) the activation marker CD69 was upregulated on CD4+ T cells and B cells (FIG. 2).

Study 2: We also observed upregulation of the molecule MHC class I (HLA-ABC) on T- and B-cells (FIG. 3), indicating an effect on antigen presentation of viral antigens.

Study 3: Stimulation of PBMC with compound 1 led to the upregulation of the co-stimulatory molecule CD80 as well as the antigen presenting molecule MHC class II (HLA-DR) on monocytes (FIG. 4).

Study 4: Monocytes differentiated into macrophages also upregulated CD80 in response to stimulation by compound 1 (FIG. 5).

Study 5: PBMCs stimulated with compound 1 for 48 h and 7 days expressed an altered cytokine profile with increased production of the immunosuppressive cytokine IL-10, measured with sandwich ELISA. This indicate an immune inhibitory effect under certain conditions (FIG. 6).

Study 6: PBMC were stimulated with compound 1 and cultured in RPMI media for 6 days in the presence of IL-2 (Miltenyi Biotechnologies) and Cell Trace Violet Dye (Invitrogen). Proliferation was measured with flow cytometry. Analysis of the immunological effect of compound 1 revealed an altered cytokine driven proliferation profile of T cells (FIG. 7).

Study 7: CMV virus specific T cell proliferation was also affected by compound 1. PBMCs from cytomegalovirus (CMV) infected donors cultured in the presence of CMV antigen and compound 1 for 6 days displayed an altered phenotype of activated CMV specific CD8+ T cells with an increased expression of IL-7 receptor a (CD127), measured with flow cytometry (FIG. 8). CD127 is crucial for T cell homeostasis, differentiation and function, and reduced expression correlates with disease severity in HIV and other chronic viral diseases (Crawley et al Sem Imm 2012).

As can be seen, compound 1 has a surprising ability to specifically activate and modify an immune response by affecting antigen presentation, co-stimulation and T cell activation and proliferation. In many of these studies, compound 2, another related macrolide erythromycin analogue with altered glycosylation, previously published in Schell et al, 2008 (as compound 20), was included and showed little or no activity in the assays.

Study 8: PBMCs from CMV infected donors cultured in the presence of CMV antigen where either untreated or exposed to compound 1 or compound 2 for 3 days. Exposure to compound 1 induced secretion of high levels of IFN-gamma, whereas antigen culture alone or antigen together with compounds 2 did not induce IFN-gamma secretion (FIG. 9).

Study 9: Macrophages from healthy donors where exposed to compounds 1 or 2 for 48 hours. Only macrophages exposed to compound 1 secreted IFN-gamma whereas untreated macrophages and macrophages exposed to compound 2 did not secrete IFN-gamma (FIG. 10). Compound 1 is therefore able to induce IFN-gamma secretion in macrophages from healthy donors.

Study 10: PBMCs and macrophages where exposed to compounds 1 or 2 for 2 days (FIG. 11). Basal expression of RANTES in PBMCs was unaffected by compound 2, whereas compound 1 induced a twofold upregulation of expression. Expression of RANTES was miniscule in macrophages, and compound 1 induced a high expression.

Study 11: PBMCs and macrophages where exposed to compounds 1 and 2 for 2 days. PBMCs and macrophages secreted IL-12p70 in response to compound 1, whereas compound 2 failed to induce secretion over untreated cells (FIG. 12).

Study 12: PBMCs, macrophages and CD4+ T cells where exposed to compounds 1 and 2 for 2 days. IL-1beta secretion was increased by compound 1 in macrophages and slightly in PBMCs while no IL-1beta was induced in CD4 +T cells (FIG. 13).

Study 13: Compound 1 was administered i.v. to C57bl/6 mice at 0.165 mg/kg to 5 mg/kg. CD25+ cell abundance was increased in animals receiving the highest dose of 5 mg/kg (FIG. 14), as was body weight in the same group (not shown).

Study 14: Compound 1 or 2 was administered i.v. to C57bl/6 mice. 24 h later the spleen was removed and MHC class I expression on CD11b+ splenocytes was assessed Compound 1 induced an increase in splenocyte cells with high MHC I expression, whereas no effect was observed in splenocytes from mice injected with compound 2.

Example 4—Assessment of Activity Against TLR2

Compounds were tested using a TLR2 reporter assay (see general methods) that measured for stimulation of the TLR2 receptor. Stimulatory effect was measured as an increase in optical density as compared to negative controls (OD) due to release of secreted alkaline phosphatase (SEAP) and is shown in table 2.

TABLE 2

|  | OD after addition of 20 µM test article | OD after addition of 10 µM test article | OD after addition of 5 µM test article |
| --- | --- | --- | --- |
| Erythromycin A | 0.045 | 0.065 | 0.035 |
| Azithromycin | 0.031 | 0.045 | 0.029 |
| Compound 2 | 0.044 | 0.010 | 0.046 |
| Compound 1 | 0.458 | 0.202 | 0.111 |
| EM703 | −0.033 | −0.024 | −0.040 |
| Compound 3 | −0.026 | −0.015 | −0.043 |

As can be seen, compound 1 stimulated TLR2 at concentrations down to 5 µM, whilst erythromycin A, azithromycin and compounds 2 and 3, related macrolide erythromycin analogues with altered glycosylation, previously published in Schell et al, 2008 (as compounds 17 and 20), showed little or no stimulation at concentrations up to 20 µM.

Example 5—Assessment of caco-2 Permeability

Compounds were tested using a standard caco-2 bidirectional permeability assay (see general methods). The data generated is shown in table 3.

TABLE 3

| | A to B permeability (Papp × $10^6$/cm · s−1) | Efflux ratio |
|---|---|---|
| Azithromycin | <0.14 | >77.6 |
| Compound 1 | 0.32 | 63.4 |
| EM703 | <0.15 | >108 |

As can be seen from the data in table 3, Compound 1 is more cell permeable and has a lower efflux ratio than both Azithromycin and EM703 (e.g. see EP1350510).

Example 6—Assessment of Metabolic Stability

The metabolic stability of the compound of the invention was assessed in a standard human microsome stability assay (see general methods). Compounds with longer halflives would be expected to have longer half-lives following dosing, which can be useful to allow less frequent dosing. Compounds with shorter half-lives could be useful for use as 'soft drugs' where the active entity degrades rapidly once entering the patient's system. The half-life of the compounds assessed in shown in table 4 below:

TABLE 4

| | T½ (minutes) |
|---|---|
| Azithromycin | 245 |
| Erythromycin | 31 |
| Compound 1 | 108 |
| EM703 | 97 |

REFERENCES

Kieser et al. 2000 Practical Streptomyces Genetics, Published by the John Innes Foundation Crawley et al. The influence of HIV on CD127 expression and its potential implications for IL-7 therapy. Semin Immunol. 2012 June; 24(3):231-40.

Gaisser et al. Analysis of seven genes from the eryAI-eryK region of the erythromycin biosynthetic gene cluster in Saccharopolyspora erythraea. Mol Gen Genet., 1997 October; 256(3):239-51.

Gaisser et al. A defined system for hybrid macrolide biosynthesis in Saccharopolyspora erythraea Mol. Micro., 2000; 36(2):391-401

Schell et al. Engineered biosynthesis of hybrid macrolide polyketides containing D-an-golosamine and D-mycaminose moieties Org. Biomol. Chem., 2008;6:3315-3327

LeMahieu et al. Glycosidic Cleavage Reactions on Erythromycin A. Preparation of Erythronolide A, J. Med. Chem., 1974, 17(9):953-956

Djokic et al. Erythromycin Series. Part 13. Synthesis and Structure Elucidation of 10-Dihydro-10-deoxo-11-methyl-11-azaerythromycin A J. Chem. Res. (5),1988; 5:152-153

Glansdorp et al. Using Chemical Probes to Investigate the Sub-Inhibitory Effects of Azithromycin, Org. Biolmol. Chem., 2008; 208(6): 4120-4124

Rowe et al. Construction of new vectors for high-level expression in actinomycetes. Gene. 1998 Aug. 17; 216(1): 215-23.

MacMicking et al. Interferon-inducible effector mechanisms in cellautonomous immunity. Nat. Rev. Immunol., 2012, 12, 367-382.

Noss et al. Toll-like receptor 2-dependent inhibition of macrophage class II MHC expression and antigen processing by 19-kDa lipoprotein of *Mycobacterium tuberculosis* J. Immunol. 2001, 167, 910-918

Ramachandra et al. Processing of *Mycobacterium tuberculosis* antigen 85B involves intraphagosomal formation of peptide-major histocompatibility complex II complexes and is inhibited by live bacilli that decrease phagosome maturation. J. Exp. Med. 2001, 194, 1421-1432

Roche et al. The ins and outs of MHC class II-mediated antigen processing and presentation. *Nature Reviews Immunology* 2015, 15, 203-216

Portal-Celhay et al. Mycobacterium tuberculosis EsxH inhibits ESCRT-dependent CD4+ T-cell activation. *Nature Microbiology* 2, Article number: 16232 (2016)

Leroux et al. Secreted Toxoplasma gondii molecules interfere with expression of MHC-II in interferon gamma-activated macrophages. *International Journal for Parasitology* 2015 45: 319-332

Zhou et al. Protection form Direct Cerebral Cryptococcus Infection by Interferon gamma-dependent Activation of Microglial Cells. *The Journal of Immunology* 2007: 178: 5753-5761

All references referred to in this application, including patent and patent applications, are incorporated herein by reference to the fullest extent possible.

The invention claimed is:

1. A compound, the compound having the structure of Formula (I):

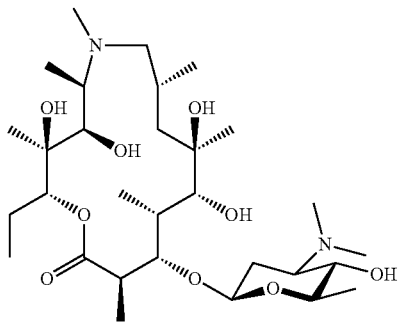

Formula (I)

or a pharmaceutically acceptable salt thereof.

2. A pharmaceutical composition comprising the compound according to claim 1.

3. The pharmaceutical composition according to claim 2, wherein the pharmaceutical composition comprises one or more pharmaceutically acceptable excipients.

4. A method for treating an intracellular infection, the method comprising administering to a human or animal subject in need thereof a therapeutically effective amount of the compound according to claim 1.

5. The method according to claim 4, wherein the intracellular infection is selected from intracellular bacterial, intracellular protozoal, and intracellular fungal infections.

6. The method according to claim 5, wherein the intracellular infection is selected from intracellular bacterial infections caused by *Mycobacterium tuberculosis*, Mycobacteria causing atypical disease, *Mycobacterium avium* and *M intracellulare* (also known as *Mycobacterium avium-intracellulare* complex, or MAC), *M kansasii*, *M marinum*, *M fortuitum*, *M gordinae*, *Mycoplasma pneumoniae*, *M genitalium*, *M hominis*, *Ureaplasma urealyticum*, *U. parvum*, *Chlamydophila pneumoniae*, and *Salmonella typhimurium*.

7. The method according to claim 5, wherein the intracellular infection is selected from intracellular protozoal infections caused by *Toxoplasma gondii*, *Plasmodium falciparum*, *P. vivax*, *Trypanosoma cruzi*, *Cryptosporidium*, and *Leishmania*.

8. The method according to claim 5, wherein the intracellular infection is selected from intracellular fungal infections caused by *Histoplasma capsulatum*, *Cryptococcus neoformans*, and *Encephalitozoon cuniculi*.

9. A method for treating or preventing a disease caused by an intracellular infection comprising administering to a human or animal subject in need thereof a therapeutically effective amount of the compound according to claim 1.

10. A method for preparing the compound as defined in claim 1, the method comprising adding an aglycone of Formula (II):

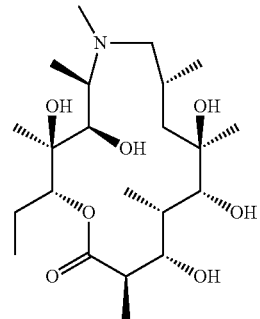

Formula (II)

to a culture of a biotransformation strain which glycosylates at the 3-hydroxyl position of the compound of Formula (II), wherein the biotransformation strain expresses glycosyltransferases with 70% or more homology to AngMII (SEQ ID NO: 1) or AngMIII (SEQ ID NO: 2).

* * * * *

SEQUENCE LISTING

```
<160> NUMBER OF SEQ ID NOS: 2

<210> SEQ ID NO 1
<211> LENGTH: 424
<212> TYPE: PRT
<213> ORGANISM: Streptomyces eurythermus
<220> FEATURE:
<223> OTHER INFORMATION: AngMII

<400> SEQUENCE: 1

Met Arg Ile Leu Leu Thr Ser Phe Ala His Asn Thr His Tyr Tyr Asn
1               5                   10                  15

Leu Val Pro Leu Gly Trp Ala Leu Arg Ala Ala Gly His Asp Val Arg
            20                  25                  30
```

-continued

```
Val Ala Ser Gln Pro Ser Leu Thr Gly Thr Ile Thr Gly Ser Gly Leu
            35                  40                  45
Thr Ala Val Pro Val Gly Asp Asp Thr Ala Ile Val Glu Leu Ile Thr
 50                  55                  60
Glu Ile Gly Asp Asp Leu Val Leu Tyr Gln Gln Gly Met Asp Phe Val
 65                  70                  75                  80
Asp Thr Arg Asp Glu Pro Leu Ser Trp Glu His Ala Leu Gly Gln Gln
                85                  90                  95
Thr Ile Met Ser Ala Met Cys Phe Ser Pro Leu Asn Gly Asp Ser Thr
                100                 105                 110
Ile Asp Asp Met Val Ala Leu Ala Arg Ser Trp Lys Pro Asp Leu Val
                115                 120                 125
Leu Trp Glu Pro Phe Thr Tyr Ala Gly Pro Val Ala His Ala Cys
 130                 135                 140
Gly Ala Ala His Ala Arg Leu Leu Trp Gly Pro Asp Val Val Leu Asn
145                 150                 155                 160
Ala Arg Arg Gln Phe Thr Arg Leu Leu Ala Glu Arg Pro Val Glu Gln
                165                 170                 175
Arg Glu Asp Pro Val Gly Glu Trp Leu Thr Trp Thr Leu Glu Arg His
                180                 185                 190
Gly Leu Ala Ala Asp Ala Asp Thr Ile Glu Glu Leu Phe Ala Gly Gln
                195                 200                 205
Trp Thr Ile Asp Pro Ser Ala Gly Ser Leu Arg Leu Pro Val Asp Gly
 210                 215                 220
Glu Val Val Pro Met Arg Phe Val Pro Tyr Asn Gly Ala Ser Val Val
225                 230                 235                 240
Pro Ala Trp Leu Ser Glu Pro Pro Ala Arg Pro Arg Val Cys Val Thr
                245                 250                 255
Leu Gly Val Ser Thr Arg Glu Thr Tyr Gly Thr Asp Gly Val Pro Phe
                260                 265                 270
His Glu Leu Leu Ala Gly Leu Ala Asp Val Asp Ala Glu Ile Val Ala
                275                 280                 285
Thr Leu Asp Ala Gly Gln Leu Pro Asp Ala Ala Gly Leu Pro Gly Asn
 290                 295                 300
Val Arg Val Val Asp Phe Val Pro Leu Asp Ala Leu Leu Pro Ser Cys
305                 310                 315                 320
Ala Ala Ile Val His His Gly Ala Gly Thr Cys Phe Thr Ala Thr
                325                 330                 335
Val His Gly Val Pro Gln Ile Val Val Ala Ser Leu Trp Asp Ala Pro
                340                 345                 350
Leu Lys Ala His Gln Leu Ala Glu Ala Gly Ala Gly Ile Ala Leu Asp
                355                 360                 365
Pro Gly Glu Leu Gly Val Asp Thr Leu Arg Gly Ala Val Val Arg Val
 370                 375                 380
Leu Glu Ser Arg Glu Met Ala Val Ala Ala Arg Arg Leu Ala Asp Glu
385                 390                 395                 400
Met Leu Ala Ala Pro Thr Pro Ala Ala Leu Val Pro Arg Leu Glu Arg
                405                 410                 415
Leu Thr Ala Ala His Arg Arg Ala
                420
```

<210> SEQ ID NO 2
<211> LENGTH: 447
<212> TYPE: PRT
<213> ORGANISM: Streptomyces eurythermus
<220> FEATURE:
<223> OTHER INFORMATION: AngMIII

<400> SEQUENCE: 2

```
Met Ser Pro Ala Pro Ala Thr Glu Asp Pro Ala Ala Gly Arg Arg
1               5                   10                  15

Leu Gln Leu Thr Arg Ala Ala Gln Trp Phe Ala Gly Thr Gln Asp Asp
                20                  25                  30

Pro Tyr Ala Leu Val Leu Arg Ala Glu Ala Thr Asp Pro Ala Pro Tyr
            35                  40                  45

Glu Glu Arg Ile Arg Ala His Gly Pro Leu Phe Arg Ser Asp Leu Leu
        50                  55                  60

Asp Thr Trp Val Thr Ala Ser Arg Ala Val Ala Asp Glu Val Ile Thr
65                  70                  75                  80

Ser Pro Ala Phe Asp Gly Leu Thr Ala Asp Gly Arg Arg Pro Gly Ala
                85                  90                  95

Arg Glu Leu Pro Leu Ser Gly Thr Ala Leu Asp Ala Asp Arg Ala Thr
            100                 105                 110

Cys Ala Arg Phe Gly Ala Leu Thr Ala Trp Gly Gly Pro Leu Leu Pro
        115                 120                 125

Ala Pro His Glu Arg Ala Leu Arg Glu Ser Ala Glu Arg Ala His
    130                 135                 140

Thr Leu Leu Asp Gly Ala Glu Ala Ala Leu Ala Ala Asp Gly Thr Val
145                 150                 155                 160

Asp Leu Val Asp Ala Tyr Ala Arg Arg Leu Pro Ala Leu Val Leu Arg
                165                 170                 175

Glu Gln Leu Gly Val Pro Glu Glu Ala Ala Thr Ala Phe Glu Asp Ala
            180                 185                 190

Leu Ala Gly Cys Arg Arg Thr Leu Asp Gly Ala Leu Cys Pro Gln Leu
        195                 200                 205

Leu Pro Asp Ala Val Ala Gly Val Arg Ala Glu Ala Ala Leu Thr Ala
    210                 215                 220

Val Leu Ala Ser Ala Leu Arg Gly Thr Pro Ala Gly Arg Ala Pro Asp
225                 230                 235                 240

Ala Val Ala Ala Arg Thr Leu Ala Val Ala Ala Glu Pro Ala
                245                 250                 255

Ala Thr Leu Val Gly Asn Ala Val Gln Glu Leu Leu Ala Arg Pro Ala
            260                 265                 270

Gln Trp Ala Glu Leu Val Arg Asp Pro Arg Leu Ala Ala Ala Val
        275                 280                 285

Thr Glu Thr Leu Arg Val Ala Pro Pro Val Arg Leu Glu Arg Arg Val
    290                 295                 300

Ala Arg Glu Asp Thr Asp Ile Ala Gly Gln Arg Leu Pro Ala Gly Gly
305                 310                 315                 320

Ser Val Val Ile Leu Val Ala Val Asn Arg Ala Pro Val Ser Ala
                325                 330                 335

Gly Ser Asp Ala Ser Thr Thr Val Pro His Ala Gly Gly Arg Pro Arg
            340                 345                 350

Thr Ser Ala Pro Ser Val Pro Ser Ala Pro Phe Asp Leu Thr Arg Pro
        355                 360                 365
```

```
Val Ala Ala Pro Gly Pro Phe Gly Leu Pro Gly Asp Leu His Phe Arg
    370             375             380

Leu Gly Gly Pro Leu Val Gly Thr Val Ala Glu Ala Ala Leu Gly Ala
385             390             395             400

Leu Ala Ala Arg Leu Pro Gly Leu Arg Ala Ala Gly Pro Ala Val Arg
            405             410             415

Arg Arg Arg Ser Pro Val Leu His Gly His Ala Arg Leu Pro Val Ala
            420             425             430

Val Ala Arg Thr Ala Arg Asp Leu Pro Ala Thr Ala Pro Arg Asn
            435             440             445
```